(12) United States Patent
Fung et al.

(10) Patent No.: US 8,010,476 B2
(45) Date of Patent: Aug. 30, 2011

(54) SYSTEM AND METHOD FOR MEDICAL PREDICTIVE MODELS USING LIKELIHOOD GAMBLE PRICING

(75) Inventors: Glenn Fung, Madison, WI (US); Phan Hong Giang, Downingtown, PA (US); Harald Steck, Phoenixville, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 735 days.

(21) Appl. No.: 12/128,947

(22) Filed: May 29, 2008

(65) Prior Publication Data
US 2008/0301077 A1 Dec. 4, 2008

Related U.S. Application Data

(60) Provisional application No. 60/941,781, filed on Jun. 4, 2007, provisional application No. 60/973,320, filed on Sep. 18, 2007, provisional application No. 61/029,695, filed on Feb. 19, 2008.

(51) Int. Cl.
*G06F 17/00* (2006.01)
*G06N 5/02* (2006.01)
(52) U.S. Cl. ........................................................ 706/46
(58) Field of Classification Search ...................... 706/62
See application file for complete search history.

(56) References Cited

U.S. PATENT DOCUMENTS

2003/0041042 A1* 2/2003 Cohen et al. .................... 706/45
2006/0234233 A1* 10/2006 Bruce et al. ..................... 435/6

OTHER PUBLICATIONS

Hammit, James, Kevin Haniger and Nicolas Treich. "The Effects of Health and Longevity on Risk Tolerance"Harvard Center for Risk Analysis Nov. 2005 [Online] Downloaded Apr. 7, 2011. http://lem.icl-lille.fr/Portals/2/seminaire/DPHammitt.pdf.*
Hey, John and Chris Orme. "Investigating Gneralizations of Expected Utility Theory using Experimental Data" Econometrica, vol. 62 No. Nov. 6, 1994. p. 1291-1326. [Online] Downloaded Apr. 7, 2011. http://www.jstor.org/stable/pdfplus/2951750.pdf?acceptTC=true.*
Giang, "A new axiomatization for likelihood gambles", 2006, Uncertainty in Artificial Intelligence: Proceedings of the $22^{nd}$ Conference (UAI-2006), Corvallis, OR, AUAI Press, pp. 192-199.

(Continued)

*Primary Examiner* — Wilbert L. Starks, Jr.
*Assistant Examiner* — Ben M Rifkin
(74) *Attorney, Agent, or Firm* — Joshua B. Ryan

(57) ABSTRACT

A method for predicting survival rates of medical patients includes providing a set D of survival data for a plurality of medical patients, providing a regression model having an associated parameter vector $\beta$, providing an example $x_0$ of a medical patient whose survival probability is to be classified, calculating a parameter vector $\hat{\beta}$ that maximizes a log-likelihood function of $\beta$ over the set of survival data, $l(\beta|D)$, wherein the log likelihood $l(\beta|D)$ is a strictly concave function of $\beta$ and is a function of the scalar $x\beta$, calculating a weight $w_0$ for example $x_0$, calculating an updated parameter vector $\beta^*$ that maximizes a function $l(\beta|D \cup \{(y_0,x_0,w_0)\})$, wherein data points $(y_0,x_0,w_0)$ augment set D, calculating a fair log likelihood ratio $\lambda^f$ from $\hat{\beta}$ and $\beta^*$ using $\lambda^f = \lambda(\beta^*|x_0) + \text{sign}(\lambda(\hat{\beta}|x_0))\{l(\hat{\beta}|D) - l(\beta^*|D)\}$, and mapping the fair log likelihood ratio $\lambda^f$ to a fair price $y_0^f$, wherein said fair price is a probability that class label $y_0$ for example $x_0$ has a value of 1.

27 Claims, 9 Drawing Sheets

OTHER PUBLICATIONS

Giang et al., "Statistical decisions using likelihood information without prior probabilities", 2002, Uncertainty in Artificial Intelligence: Proceedings of the Eighteenth Conference (UAI-2002), San Francisco, CA, Morgan Kaufmann, pp. 170-178.

Giang et al., "Decision making on the sole basis of statistical likelihood", 2005, Artificial Intelligence, 165, pp. 137-163.

Kaiserman et al., "Forecasting the Prognosis of Choroidal Melanoma with an Artificial Neural Network", Ophthalmology, J.B. Lippincott Col, Philadelphia, PA, vol. 112, No. 9, Sep. 1, 2005.

Giang et al., "A new axiomatization for likelihood gambles", Proceedings of the 22nd Annual Conference on Uncertainty in Artificial Intelligence, AUAI Press, 2006, pp. 192-199.

Fung et al., "Improving medical predictive models via Likelihood Gamble Pricing", Proceedings of the ICML/UAI/COLT Workshop on Machine Learning for Health-Care-Applications, 2008, pp. 1-6.

International Search Report including Notification of Transmittal of the International Search Report, International Search Report, and Written Opinion of the International Searching Authority, May 2, 2009.

* cited by examiner

| Data No. | Launch date | Temperature | Nr. incidents | Failure status |
|---|---|---|---|---|
| 1 | 1/24/1985 | 53 | 2 | 1 |
| 2 | 2/3/1984 | 57 | 1 | 1 |
| 3 | 1/12/1986 | 58 | 1 | 1 |
| 4 | 4/6/1984 | 63 | 1 | 1 |
| 5 | 4/12/1981 | 66 | 0 | 0 |
| 6 | 4/4/1983 | 67 | 0 | 0 |
| 7 | 11/8/1984 | 67 | 0 | 0 |
| 8 | 4/12/1985 | 67 | 0 | 0 |
| 9 | 11/11/1982 | 68 | 0 | 0 |
| 10 | 3/22/1982 | 69 | 0 | 0 |
| 11 | 11/12/1981 | 70 | 1 | 1 |
| 12 | 11/28/1983 | 70 | 0 | 0 |
| 13 | 8/30/1984 | 70 | 1 | 1 |
| 14 | 6/17/1985 | 70 | 0 | 0 |
| 15 | 6/18/1983 | 72 | 0 | 0 |
| 16 | 8/30/1983 | 73 | 0 | 0 |
| 17 | 4/29/1985 | 75 | 0 | 0 |
| 18 | 10/30/1985 | 75 | 2 | 1 |
| 19 | 8/27/1985 | 76 | 0 | 0 |
| 20 | 11/26/1985 | 76 | 0 | 0 |
| 21 | 10/5/1984 | 78 | 0 | 0 |
| 22 | 10/3/1985 | 79 | 0 | 0 |
| 23 | 7/29/1985 | 81 | 0 | 0 |

SYSTEM AND METHOD FOR MEDICAL PREDICTIVE MODELS USING LIKELIHOOD GAMBLE PRICING

CROSS REFERENCE TO RELATED UNITED STATES APPLICATIONS

This application claims priority from "Likelihood Gamble Pricing Approach to Classification", U.S. Provisional Application No. 60/941,781 of Fung, et al., filed Jun. 4, 2007, "Classification Method that Uses Hypothetical Labels for Testing Data", U.S. Provisional Application No. 60/973,320 of Giang, et al., filed Sep. 18, 2007, and "Improved Prediction of Outcome", U.S. Provisional Application No. 61/029,695 of Giang, et al., filed Feb. 19, 2008, the contents of all of which are herein incorporated by reference in their entirety.

TECHNICAL FIELD

This disclosure is directed to the development and validation of improved predictive models for survival and radiation induced side-effects of non-small cell lung cancer (NSCLC) patients, treated with (chemo) radiotherapy.

DISCUSSION OF THE RELATED ART

Radiotherapy, combined with chemotherapy, is the treatment of choice for a large group of lung cancer patients. Radiotherapy is not restricted to patients with mediastinal lymph node metastasis, but is also indicated for patients who are inoperable because of their physical condition. Improved radiotherapy treatment techniques allowed an increase of the radiation dose delivered to the tumor, while keeping the occurrence of treatment-induced side-effects, like pneumonitis or esophagitis, to a minimum. Moreover, it has been found that combining radiotherapy with chemotherapy can improve outcomes even further. Several effective chemo radiation schemes are being applied. These developments have led to improved outcome in terms of survival time while minimizing the occurrence of treatment-related side-effects.

Given the multitude of chemo radiation schemes, it would be desirable to choose the most effective one for each individual patient. The relationship between patient/tumor characteristics, the applied treatment regime and the outcome is not well understood in the medical field to date. For this reason, it is desirable to learn predictive models that can estimate the outcome, both survival and side-effects, for an individual patient under the various treatment options. Given sufficient prediction accuracy, these models can then be used to optimize the treatment of each individual patient, which is the goal of personalized medicine. These models can thus assist the medical doctor with decision support at the point of care.

Although research has been conducted regarding training such models from existing data, an accurate estimation of the survival probability to offer assistance for treatment decision-making for an individual patient is currently not available. Given sufficiently accurate predictions of these models, they can then be used to optimize the treatment of each individual patient, which is the goal of personalized medicine. This motivates a need for the creation of improved robust predictive models that take into account the available information about the patient prior to (and then during) treatment: tumor characteristics, clinical and demographic data as well as information on treatment alternatives.

A probabilistic classification task can be formulated as the task of label assignment to a testing point given a set of labeled training points. Training data is a set of labeled data points $D=\{(y_i, x_i) | 1 \leq i \leq n\}$ where $y_i \in \{0, 1\}$ are called labels for data points $x_i$ which are vectors in a multidimensional real space called feature values. The goal is to predict the label $y_0$ for a new testing point $x_0$ assuming that the probability law that governs the relationship between label and feature values is the same for training and testing data points.

An essential structural assumption is that the probability law that governs the relationship between explanatory variables (coordinates of data points) and explained variable (label) is invariant for training and testing points. Moreover, this function belongs to a certain class of models. For example in a popular Generalized Liner Model (GLM) method one makes a postulate that actual labels are observed instances of Bernoulli variable whose mean is a function of linear combination of feature values, $$Pr(Y=1|w,x)=f(x'\cdot w)$$

where x' is the transpose of feature vector x, w is a vector of coefficients and $x'\cdot w$ is the inner product. Each model is identified by the coefficient vector. In particular if f is a logistic function $f(z)=(1+\exp(-z))^{-1}$ then one has a logistic regression. This structural assumption makes it possible to leverage the training data in order to predict the label of the testing point. Frequently the probability with which the label is predicted is of greater interest than the label itself.

Most of available classification methods select a model w* by maximizing the log likelihood with some regularization term and then use the selected model to predict the probability of a label for feature vector $x_0$. The log likelihood for a model w given data D is the following quantity:

$$l(w|D) = \sum_{i=1}^{n} \log Pr(Y = y_i | w, x_i),$$

$$w^* = \arg\max_w (l(w|D) + \text{regularization}),$$

$$Pr(Y = 1 | w^*, x_0) = f(x_0' \cdot w^*).$$

Most statistical packages have a built-in MLE implementation that uses a maximum likelihood with no regularization.

Clearly, the crux of the task is that the probability law that governs the relationship between explanatory variables and explained variable is unknown except that it belongs to an assumed class and each model has its own prediction of label probability. Consequently, the handling of the model uncertainty is an issue. Traditionally, there are two major approaches: model selection and model averaging.

The model selection approach tries to identify one model in the class and uses it as the proxy for the underlying true model to predict the label. Two concerns for a model are the accuracy/fitness to the training data and the generalizability/robustness on unseen data. The fitness can be measured by the probability with which the model predicts the training data. This quantity is also known as the likelihood of the model. Focusing exclusively on accuracy for training data can lead to overfitting because more complex models can fit better for training data but their performance for testing data can be poor. Various criteria for model selection are attempts to strike a right balance between fitness and complexity.

In a Bayesian model averaging approach the label probabilities from individual models are averaged with weights equal to the posterior probabilities of the models. The posteriors are obtained via Bayes' theorem from the likelihood given the training data and some prior probability function. When the prior, and consequently, the posterior probabilities of models are known, the Bayesian solution has been shown to be optimal. This optimality is a consequence of a fundamental result of the Bayesian decision theory: if the behavior of a decision maker satisfies a number of rational postulates then an action of uncertain outcomes must be evaluated by the average of utilities of the outcomes weighted with probabilities of their realization (expected utility). The link between statistical theory and decision theory has been long established. The difference is that in model selection, the robustness concern is addressed by controlling model complexity while in model averaging this concern is addressed by diversifying the basis of prediction.

A difficulty with Bayesian approach is in the assumption of prior probability. Proponents of Bayesianism argue that this prior comes from either a decision maker's a priori personal knowledge or the summary of previous and similar studies.

The basic idea behind Bayesian decision theory and the difficulty with the prior assumption motivate a decision theory that directly uses likelihood as an uncertainty measure. The elementary object of this theory is the notion of "likelihood gamble". Each model is associated with a two quantities: a likelihood awarded by the training data and a label probability for the testing point predicted by the model. A likelihood gamble is the set of such pairs, one for each model in the class. It turns out that, as it is the case for Bayesian decision theory, if decision maker's behavior in dealing with likelihood gambles satisfies a number of rational postulates, then it can be proved that likelihood gambles must be evaluated by a well defined construct.

SUMMARY OF THE INVENTION

Exemplary embodiments of the invention as described herein generally include methods and systems for improved predictive models obtained by using a Likelihood gamble pricing (LGP), which is a decision-theoretic approach to statistical inference that combines the likelihood principle of statistics with Von Neumann-Morgensterns axiomatic approach to decision making. The regularization induced by the LPG approach produces better probabilistic predictions than both the unregularized and the regularized (by the standard 2-norm regularization) widely used logistic regression approaches. In several survival and side effects models, a Likelihood Gamble Pricing (LGP) approach according to an embodiment of the invention provides excellent generalization, yielding more accurate and more robust predictions than other standard machine learning approaches.

An LGP approach according to an embodiment of the invention provides a new way for making predictions without learning a specific model by considering the task of predicting the probability of a binary label, such as the presence of side-effect or survival at 2-years, of a new example in the light of the available training data. In an LPG approach according to an embodiment of the invention, the (labeled) training data and the (unlabeled) new example are combined in a principled manner to achieve a regularized prediction of the probability of the unknown label. The task of assigning a label to a data point is formulated as a "likelihood gamble" whose price is interpreted as the probability of the label. Informally, a method according to an embodiment of the invention leverages the information available from both the training set and a given testing point to improve predictions by adding extra information when the training set is small and by avoiding overfitting when the training set is large. This regularized prediction is achieved by solving two unregularized maximum likelihood tasks.

LGP approach according to an embodiment of the invention can be applied to any generalized linear model. Embodiments of the invention are applied to the logistic regression model and Gaussian regression model. An LGP prediction algorithm is investigated by contrasting it against a standard maximum likelihood method (MLE). Like MLE, LGP is asymptotically consistent, but LGP provides a remedy for a number of known shortcomings of MLE, such as instability in case of a flat likelihood function and underestimation of the probabilities of rare events.

In a further embodiment of the invention, an LGP decision-theoretic approach is examined from a statistical perspective, and several properties are derived: (1) combining an (unlabeled) example with labeled training data as to predict its class label; (2) comparing LGP to Bayesian statistics and to transductive inference; and (3) providing an approximate solution to LGP that is computationally efficient and yields a regularized prediction of the class label by solving two standard (unregularized) maximum likelihood problems.

According to another embodiment of the invention, a classification algorithm uses hypothetical labels for data points that need to be classified to compute the probability of label from the difference of log likelihoods computed for two hypothetical data sets obtained by augmenting the given labeled training data set with hypothetically labeled testing data. A prototype implementation shows superior accuracy compared with traditional MLE method.

According to another embodiment of the invention, a classification algorithm predicts discrete or continuous-valued properties, such as the probability of 2-year survival of a cancer patient, the probability of re-occurrence of cancer in a patient after a certain time period, or the risk of suffering from a treatment-related side-effect.

Empirical results in several publicly available datasets confirm that al LGP classification approach according to an embodiment of the invention can produce more accurate and robust predictions than a standard classification method. On simulated data, it is shown that an LGP approach according to an embodiment of the invention outperforms MLE with respect to the mean square error and KL divergence, especially in cases of small training data. This result validates both a theory constructed from basic rational postulates and an efficient algorithm in situations where the training data is scarce. Experiments on UCI data indicate that an LGP approach according to an embodiment of the invention generalizes easily, yielding more accurate and more robust predictions than standard machine learning approaches.

According to an aspect of the invention, there is provided a method for predicting survival rates of medical patients, the method including providing a set D of survival data for a plurality of medical patients having a same condition, providing a regression model, said model having an associated parameter vector $\beta$, providing an example $x_0$ of a medical patient whose survival probability is to be classified, calculating a parameter vector $\hat{\beta}$ that maximizes a log-likelihood function of $\beta$ over the set of survival data, $l(\beta|D)$, wherein the log likelihood $l(\beta|D)$ is a strictly concave function of $\beta$ and is a function of the scalar $x\beta$, calculating a weight $w_0$ for example $x_0$, calculating an updated parameter vector $\beta^*$ defined as the parameter vector $\beta$ that maximizes a function $l(\beta|D \cup \{(y_0,x_0,w_0)\})$ wherein data points $(y_0,x_0,w_0)$ augment said set D, calculating a fair log likelihood ratio $\lambda^f$ from $\hat{\beta}$ and $\beta^*$ using $\lambda^f = \lambda(\beta^*|x_0) + \text{sign}(\lambda(\hat{\beta}|x_0))\{l(\hat{\beta}|D) - l(\beta^*|D)\}$, and mapping the fair log likelihood ratio $\lambda^f$ to a fair price $y_0^f$, wherein said fair price is a probability that class label $y_0$ for example $x_0$ has a value of 1.

According to a further aspect of the invention, the weight $w_0$ is calculated from $$w_\diamond = -\left.\frac{\frac{\partial}{\partial(x_\diamond\beta)}|\lambda(\beta|x_\diamond)|}{\frac{\partial}{\partial(x_\diamond\beta)}l(\beta|(y_\diamond,x_\diamond,w_\diamond=1))}\right|_{\beta=\hat{\beta}},$$

wherein $\lambda(\beta|x_0)$ is a log-likelihood ratio of a likelihood that a class label $y_0$ has a value of 1 over a likelihood that a class label $y_0$ has a value of 0, wherein said log-likelihood-ratio is an affine function of the scalar $x\beta$.

According to a further aspect of the invention, the regression model is a logistic regression model with a probability of label y being 1 is $$p(y=1|x,\beta) = \frac{1}{1+\exp(-\lambda(\beta|x))},$$

wherein $\lambda(\beta|x) = x\beta$.

According to a further aspect of the invention, the log-likelihood of $\beta$ is $$l(\beta|D) = \sum_{i=1}^{N} w_i\{(y_i-1)x_i\beta - \log(1+\exp(-x_i\beta))\}.$$

According to a further aspect of the invention, the weight $w_0$ is calculated from $$w_\diamond = \frac{-\text{sign}(x_\diamond\hat{\beta})}{y_\diamond - 1 + \frac{1}{1+\exp(x_\diamond\hat{\beta})}}.$$

According to a further aspect of the invention, the fair log likelihood ratio $\lambda^f$ is $\lambda^f = x_0\beta^* + \text{sign}(x_0\hat{\beta})[l(\hat{\beta}|D) - l(\beta^*|D)]$.

According to a further aspect of the invention, the fair price is $$y_\diamond^f = \frac{1}{1+\exp(-\lambda^f)}.$$

According to a further aspect of the invention, the regression model is a Gaussian regression model with two clusters having a Gaussian distribution for either class, $N(0,\sigma^2)$ and $N(1,\sigma^2)$, wherein $\sigma^2$ is a standard deviation.

According to a further aspect of the invention, the log-likelihood of $\beta$ is $$l(\beta|D) = -\sum_{i=1}^{N} w_i(x_i\beta - y_i)^2/\sigma^2.$$

According to a further aspect of the invention, the weight $w_0$ is calculated from $$w_\diamond = \frac{-\text{sign}(2x_\diamond\hat{\beta} - 1)}{x_\diamond\hat{\beta} - y_\diamond}.$$

According to a further aspect of the invention, the fair log likelihood ratio $\lambda^f$ is $$\lambda^f = \log\frac{p(y=1|x,\beta)}{p(y=0|x,\beta)}$$
$$= (2x\beta - 1)/\sigma^2.$$

According to a further aspect of the invention, the fair price is $$y_\diamond^f = 1 + \lambda^f \sigma^2/2$$
$$= x_\diamond\beta^* + \frac{\text{sign}(2x_\diamond\hat{\beta} - 1)}{2}(l(\hat{\beta}|D) - l(\beta^*|D)).$$

According to a further aspect of the invention, the weight $w_0=2$, and said updated parameter vector $\beta^*$ is determined by maximizing $l(\beta|D \cup \{(1,x_0,1),(0,x_0,1)\})$, wherein $(1,x_0,1),(0,x_0,1)$ are data points augmenting said set D.

According to another aspect of the invention, there is provided a program storage device readable by a computer, tangibly embodying a program of instructions executable by the computer to perform the method steps for predicting survival rates of medical patients.

DETAILED DESCRIPTION OF EXEMPLARY EMBODIMENTS

Figures 1, 2:
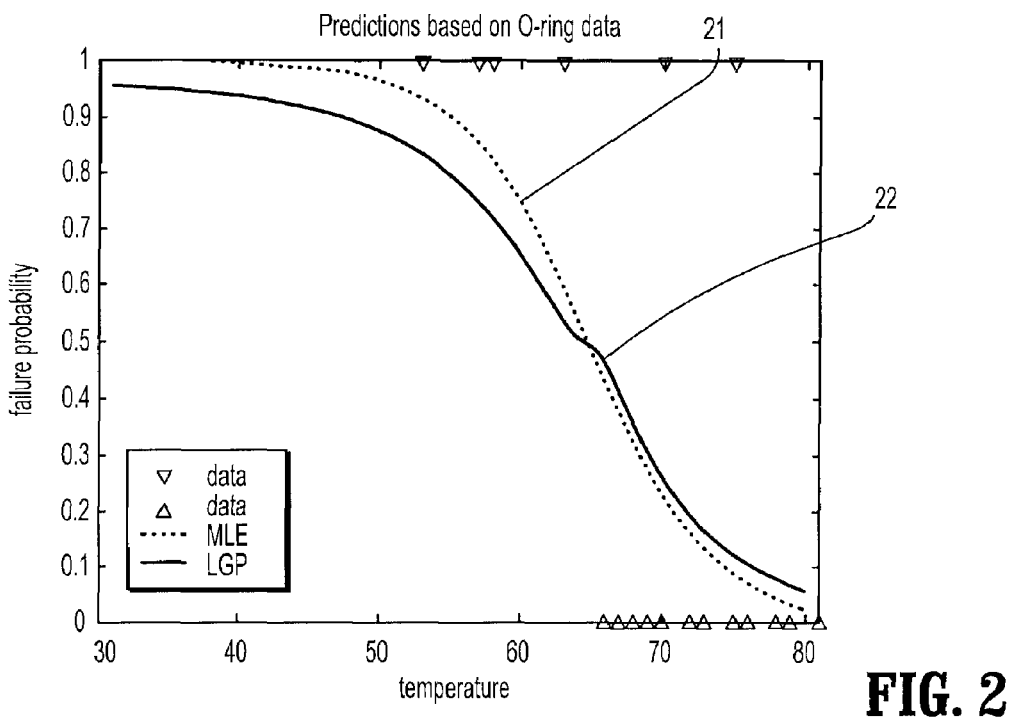
FIG. 1 is a table of space shuttle O-ring data.
FIG. 2 is a graph of MLE and LGP curves computed for the temperature range of 31–81° F., according to an embodiment of the invention.

Exemplary embodiments of the invention as described herein generally include systems and methods for the classification of cancer patient survival data based on a likelihood gamble pricing approach. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

Likelihood Gamble Pricing

Likelihood gamble pricing is a combination of the likelihood principle of statistics with the von Neumaun-Morgenstern axiomatic approach to decision making. It takes from von Neumann and Morgenstern the idea that decision theory under uncertainty should be constructed from basic rational axioms and fuses with a fundamental idea from statistics that a likelihood function represents all information from observed data.

Formally, consider an ambiguous situation described by a tuple $(X, Y, \Theta, A, D)$. $X, Y$ are the variables describing a phenomenon of interest. X is a predictor variable whose values can be observed. Y is a response variable whose values determine the utility of actions. $\Theta$ denotes the set of probabilistic models over X, Y that encode knowledge about the phenomenon. A is the set of actions that are functions from the domain of utility variable Y to the unit interval [0, 1] representing risk-adjusted utility. Finally, the data gathered is denoted by D. Although the term "model" is often used in the literature to denote a family of probability functions sharing a common functional form, the more specific term "parametric model" is used herein for this concept and the term "model" or "complete model" is reserved for a fully specified probability function.

Given an action $a \in A$, each model $\theta \in \Theta$ is associated with two quantities: the likelihood of the model $Pr_\theta(D)$ and the expected utility of the action conditional on the model $E_\theta[a] = \int_y dy\, a(y) Pr_\theta(y)$. We put these quantities together and have a likelihood prospect, denoted as $(Pr_\theta(D):E_\theta[a])$. An action in presence of multiple models $\Theta$ and observed data D is described by a collection of prospects. And since likelihood functions are determined up to a proportional constant, a likelihood function can be normalized so that the maximum is 1:

$$L_\theta = Pr_\theta(D)/Pr_\Theta(D) \quad (1)$$

where $Pr_\Theta(D) \equiv \max_{\theta \in \Theta}\{Pr_\theta(D)\}$.

Thus, $\max_{\theta \in \Theta}\{L_\theta\}=1$. A set of prospects with normalized likelihoods $\{(L_\theta:E_\theta[a])|\theta \in \Theta\}$ is called a likelihood gamble. Formally, Definition 1: The set of likelihood gambles G is defined recursively as follows.

(i) $[0, 1] \subset G$;

(ii) Let I be a set of indices, $l_i \in [0, 1]$, $\max_{i \in I} l_i = 1$ and $g_i \in G$ for $i \in I$, then $\{(l_i:g_i)|i \in I\} \in G$; and (iii) Nothing else belongs to G.

This definition makes the set of likelihood gambles a mixture set. A number $x \in [0, 1]$ is called a constant gamble. It represents an action a in ambiguity-free situations where only one model is possible i.e., $\Theta = \{Pr_\theta\}$, and x is the expected utility of a with respect to $Pr_\theta$ Consider a preference relation $\succeq$ over likelihood gambles. A strict preference $\succ$ and indifference $\sim$ relations are defined as usual: $g_1 \succ g_2$ iff $g_1 \succeq g_2 \hat{} g_2 \not\succeq g_1$, and $g_1 \sim g_2$ iff $g_1 \succeq g_2 \hat{} g_2 \succeq g_1$.

It is assumed that $\succeq$ satisfies the following axioms:

(A1) Weak order: $\succeq$ is complete and transitive.

(A2) Archimedean axiom: If $f \succ g \succ h$ then there exist normalized likelihood vectors $(a_i)$ and $(b_i)$ such that $\{a_1:f, a_2:h\} \succ g$ and $g \succ \{b_1:f, b_2:h\}$.

(A3) Independence: Suppose $f \succeq g$ and let $(a_i)$ be a normalized likelihood vector, then for any h, $\{a_1:f, a_2:h\} \succeq \{a_1:g, a_2:h\}$.

(A4) Compound gamble: Suppose $f_1=\{b_{1i}:f_{1i}|i \in I\}$, $f_2=\{b_{2j}:f_{2j}|j \in J\}$, then
$\{a_1:f_1, a_2:f_2\} \sim \{a_1 b_{1i}:f_{1i}|i \in I\} \cup \{a_2 b_{2j}:f_{2j}|j \in J\}$.

(A5) Idempotence: $\{a_i:f|i \in I\} \sim f$ for any set I.

(A6) Numerical order: For f, $h \in [0, 1]$, $f \succeq h$ iff $f \geq h$.

The measure of uncertainty for these axioms is the statistical likelihood.

Definition 2:

(i) $B = \{(\alpha,\beta)|0 \leq \alpha, \beta \leq 1, \max(\alpha,\beta)=1\}$ is a set of 2-dimensional vectors represented by points in the top and right borders of the unit square.

(ii) For scalar $a_i, b_i, c \in [0,1]$, the operations max and product are defined as $$\max((a_1,b_1),(a_2,b_2)) \equiv (\max(a_1,a_2),\max(b_1,b_2)) \quad (2)$$

$$c(a_1,b_1) \equiv (ca_1,cb_1) \quad (3)$$

(iii) An order $\succeq$ on B is defined as $(a_1,b_1) \succeq (a_2,b_2)$ iff $a_1 \geq a_2$ and $b_1 \geq b_2$.

Definition 3: A preference relation $\succeq$ is represented by a utility function $U:G \rightarrow B$ whenever $g \succeq g'$ iff $U(g) \succeq U(g')$ There is the following representation theorem.

Theorem 4 (Representation Theorem): If $\succeq$ satisfies axioms A1-A6, then it is represented by a utility function that maps likelihood gambles to B such that $$U(\{l_\theta / v_\theta \mid \theta \in \Theta\}) = \max_{\theta \in \Theta}(l_\theta U(v_\theta)). \quad (4)$$

This utility function representation is no longer a real line but a set of 2-dimensional vectors.

Definition 5: A number $0 \leq x \leq 1$ is called the price or the ambiguity-free equivalence of gamble g if $g \sim x$.

The representation theorem suggests a procedure for determining the price of a likelihood gamble. First, calculate the gamble's 2-dimensional utility according to EQ. (4) and then find a constant gamble having the same 2-dimensional utility. Indeed, suppose $U(g)=(\alpha,\beta)=U(v)$ where v is a number in the unit inter-val. From the representation theorem, it follows that $g \sim \{\alpha/1, \beta/0\} \sim v$. By transitivity, $g \sim v$. Therefore, v is the price of gamble g.

Gambles of the form $\{\alpha/1, \beta/0\}$ are called a canonical gambles. $\{\alpha/1, \beta/0\}$ describes an action f in a simple situation where the class of models consists of just two elements $\Theta=\{\theta_1, \theta_2\}$ with corresponding normalized likelihoods $\alpha, \beta$. The risk-adjusted expected utility of f is 1 under $\theta_1$ and 0 under $\theta_2$. It can be shown that indifference $v \sim \{\alpha/1, \beta/0\}$ implies the following equation that relates values v and $\alpha, \beta$.

$$\text{logit}(v) = \ln(\alpha/\beta) + c, \quad (5)$$

where logit(z)=ln(z/(z−1)) for z∈(0, 1) and c is a parameter representing ambiguity averse degree of a decision maker. Intuitively c is the price that the decision maker would pay for a "fair" canonical gamble {1/1, 1/0} where data equally supports each of two possible models.

Given c, EQ. (5) can be solved for $\alpha$, $\beta$ taking into account max($\alpha$, $\beta$)=1:

$$\begin{cases} \alpha = \min(1, \exp(\text{logit}(v) - c)), \\ \beta = \min(1, \exp(-\text{logit}(v) + c)). \end{cases} \quad (6)$$

Here it is assumed c=0. Then EQ. (6) can be rewritten as $$\begin{cases} \ln(\alpha) = \min(0, \ln(v) - \ln(1 - v)), \\ \ln(\beta) = \min(0, \ln(1 - v) - \ln(v)). \end{cases} \quad (7)$$

A simple likelihood gamble pricing (LGP) algorithm according to an embodiment of the invention to find price for a gamble $\{l_\theta/v_\theta | \theta \in \Theta\}$ is as follows,
1. Solve 2 maximization tasks:

$$\ln(\alpha^*) = \max_{\theta \in \Theta}(\ln(l_\theta) + \ln(\alpha_\theta)), \quad (8)$$

$$\ln(\beta^*) = \max_{\theta \in \Theta}(\ln(l_\theta) + \ln(\beta_\theta)) \quad (9)$$

where $\ln(\alpha_\theta)$, $\ln(\beta_\theta)$ are given in EQ. (7). $U(v_\theta)=(\alpha_\theta, \beta_\theta)$.
2. Defining $A = \ln(\alpha^*) - \ln(\beta^*)$, the gamble's price is $$v = \frac{\exp(A)}{1 + \exp(A)} = \frac{1}{1 + \exp(-A)} = \frac{\alpha^*}{\alpha^* + \beta^*}. \quad (10)$$

Note that the two maximization tasks (8) and (9) are a consequence of EQ. (4) and EQ. (10) follows from EQ. (5).

The relationship between constant gambles and their utilities is formalized by a function t mapping the unit interval [0, 1] into B. The left and the right components of t(v) are denoted by $t_\alpha(v)$ and $t_\beta(v)$, i.e., $t(v)=(t_\alpha(v), t_\beta(v))$. The intuitive meaning of t is to convey the indifference relation. For instance, t(0.4)=(0.6, 1) means that the decision maker is indifferent between getting 0.4 and playing a likelihood gamble {0.6:1, 1:0} that delivers utility 1 with (relative) likelihood 0.6 and utility 0 with likelihood 1. One assumption about t is the strictly positive monotonicity of the ratio $t_\alpha(v)/t_\beta(v)$ and of v. This allows one to define the inverse $t^{-1}$.

With the help of t, the pricing formula for likelihood gambles is obtained by using the definition of max in EQS. (2) and (4). Suppose v is the price of $\{L_i : v_i | i \in I\}$, then $$v = t^{-1}\left(\left(\max_{i \in I} L_i \cdot t_\alpha(v_i), \max_{i \in I} L_i \cdot t_\beta(v_i)\right)\right) \quad (11)$$

The pricing formula calls for solving two maximization tasks. One maximizes the product of the likelihood and the left component of t(v), the other maximizes the product of the likelihood and the right component of t(v). The obtained 2-dimensional utility is converted into a scalar utility by the inverse of t.

To summarize, there is a formula for prediction on the basis of the observed data. This formula, derived from rational postulates, offers a new prediction paradigm which is distinct from traditional approaches such as model selection and Bayesian model averaging. In the model selection approach, the observed data is used to select the best fitted model which is then used for prediction. In Bayesian model averaging, predictions by individual models are "averaged" with posterior model probability calculated from some prior model probability and the likelihood function computed from the data. As reviewed above, the prediction according to LGP involves neither a specific selected model nor a posterior model probability. To address the issue of what benefits are offered by an LGP approach according to an embodiment of the invention, the pricing formula (11) will be used to solve for a logistic regression model.

The following notation convention will be used: upper case letters denote random variables; lower case letters are used for their instantiations; a colon ":" is used to separate likelihoods from values in likelihood prospects and gambles; calligraphic letters are used for sets. L denotes (normalized) likelihoods, and l the log likelihoods. By default, the observed data D on which (log) likelihoods are based is omitted. w and its indexed versions denote models, or their coefficient vectors. $x_i$ denote points of training data; x (without index) denotes the point where prediction is needed. ĥ and g denote predictions by MLE and LGP, respectively.

Gamble View of the Logistic Model

The logistic regression model is a workhorse in statistics with applications in categorical data analysis and machine leaning. The predictor X is a multi-dimensional random variable. Each component X(i) of X will be referred to as a (input) feature. It is often assumed for convenience that the first feature is a constant X(1)=1. The response (class) Y is a discrete random variable. The focus hereinafter will be on the binary case where Y can take values −1 or 1. An instance of X will be arranged as a row vector x. The data generation process is such that the logarithm of the odds of classes is a linear combination of feature values. Equivalently, the class probability conditional on x and coefficient vector w is given by $$Pr(y|x,w) = (1 + \exp(-yxw))^{-1}, \quad (12)$$

where w is a column coefficient vector. Thus, $$\log(Pr(y=1|x,w)/Pr(y=-1|x,w)) = xw.$$

Consider the following forecast problem. Given the data generation process of logistic model and a random sample of labeled data $D=\{(x_i, y_i) | 1 \leq i \leq n\}$, it is desired to predict the class of a given point x.

Normally, this forecast task is not solved directly, but rather is formulated as a by-product of the task of estimating the coefficient vector w. The standard approach is to estimate ŵ via maximum likelihood. The estimated probability concerning a test-example x is then $Pr(Y=1|x, ŵ) = (1 + \exp(-xŵ))^{-1}$.

From the likelihood gamble point of view, the forecast task for given x is represented by the following gamble:

$$\{L_D(w) : Pr(y=1|x,w) | w \in R^m\}, \quad (13)$$

where $L_D(w)$ is the normalized likelihood of w given the data D. This will be referred to as the forecast gamble.

Some basic facts about the logistic model will now be reviewed. The log likelihood function is $$l(w) = \log L_D(w) \quad (14)$$

$$= -\sum_{i=1}^{n} \log(1 + \exp(-y_i x_i w)).$$

It is also well known that l(w) is concave.

Before EQ. (11) can be used, the conversion function t needs to be determined. To do so, recall that the semantics of t(v) is such that gamble $\{t_\alpha(v):1, t_\beta(v):0\}$ is considered equivalent to v by the decision maker. In the case of the logistic model, v is the probability $Pr(y=1|x,w)$. A natural condition that can be imposed is to equalize the likelihood ratio and the posterior odds. That is $t_\alpha(v)/t_\beta(v)=v/(1-v)$. Together with the normalization condition $\max(t_\alpha(v), t_\beta(v))=1$, this leads to the solution $$\begin{cases} t_\alpha(v) = \min(1, v/(1-v)) \\ t_\beta(v) = \min(1, (1-v)/v) \end{cases} \quad (15)$$

for $0<v<1$. For the boundary cases $t_\alpha(1)=1$, $t_\beta(1)=0$, $t_\alpha(0)=0$ and $t_\beta(0)=1$.

The inverse function $t^{-1}$ is then $$t^{-1}((\alpha, \beta)) = \frac{\alpha}{\alpha + \beta} = \frac{1}{1 + \beta/\alpha}. \quad (16)$$

Gamble (13) can be priced by formula (11) when plugging in EQS. (12), (14), (15) and (16).

Next, some simplifications are outlined. Notice that, instead of maximizing the product, it is more convenient to maximize its logarithm:

$$\log(L_D(w)t_\alpha(Pr(y=1|x,w)))=l(w)+\min(0,xw),$$

$$\log(L_D(w)t_\beta(Pr(y=_1|x,w)))=l(w)+\min(0,-xw),$$

where $l(w)=\log(L_D(w))$ because of EQ. (15), and $$\log(Pr(y=1|x,w)/Pr(y=-1|x,w))=xw.$$

$$\log(Pr(y=-1|x,w)/Pr(y=1|x,w))=-xw.$$

Thus, the price for the forecast gamble can be found in two steps:

1. Solve the 2 maximization tasks:

$$a=\max_w(l(w)+\min(0,xw)) \quad (17)$$

$$b=\max_w(l(w)+\min(0,-xw)) \quad (18)$$

2. The gamble's price is then $p=(1+\exp(-a+b))^{-1}$.

Denote the value p found by an LGP algorithm according to an embodiment of the invention by $g_D(x)$. In the following, its properties are investigated mostly by contrasting it with the maximum likelihood solution $\hat{h}_D(x)$.

Denote the solutions of (17) and (18) as well as the maximum likelihood solution as follows:

$$\hat{w}_a = \arg\max_w(l(w) + \min(0, xw)), \quad (19)$$

$$\hat{w}_b = \arg\max_w(l(w) + \min(0, -xw)), \quad (20)$$

$$\hat{w} = \arg\max_w(l(w)). \quad (21)$$

It is possible that these maximization problems may have more than one solution. In this case, $\hat{w}$ denotes any point where the log likelihood is maximal.

Theorem 6: For a, b found by EQS. (17) and (18): either $a=l(\hat{w})$ or $b=l(\hat{w})$.

Proof: By definition of $\hat{w}$, $\hat{w}_a$ and $\hat{w}_b$, for any w, there is $$a \geq l(w)+\min(0,xw), \quad (22)$$

$$b \geq l(w)+\min(0,-xw), \quad (23)$$

$$l(\hat{w}) \geq l(w). \quad (24)$$

Due to EQ. (24), $l(\hat{w})\geq l(w)$ and $l(\hat{w})\geq l(w)$. For scalar $x\hat{w}$, either $x\hat{w}\geq 0$ or $x\hat{w}\leq 0$. If $x\hat{w}\geq 0$, $l(\hat{w})+\min(0,x\hat{w})=l(\hat{w})$. One has $l(\hat{w})\geq l(\hat{w}_a)\geq a\geq l(\hat{w})+\min(0,x\hat{w})=l(\hat{w})$. Thus, $l(\hat{w})=a$. In case $x\hat{w}\leq 0$, one can show $l(\hat{w})=b$ analogously.

From this theorem, a second version of LGP can be formulated that offers some savings when computing the prices of many forecast gambles on the same data set. If $x\hat{w}\geq 0$, then $a=l(\hat{w})$ and $$b=\max_w(l(w)-xw) \text{ such that } xw\geq 0. \quad (25)$$

Otherwise if $x\hat{w}\leq 0$, then $b=l(\hat{w})$ and $$a=\max_w(l(w)+xw) \text{ such that } xw\leq 0. \quad (26)$$

Theorem 7: Suppose $g_D(x)$ is the price of the forecast gamble and $\hat{h}_D(x)$ is an MLE prediction, then $$(g_D(x)-0.5)(\hat{h}_D(x)-0.5)\geq 0,$$

$$(g_D(x)-\hat{h}_D(x))(\hat{h}_D(x)-0.5)\leq 0.$$

Proof: It is necessary to show that (a) if $\hat{h}_D(x)\geq 0.5$, then $\hat{h}_D(x)\geq g_D(x)\geq 0.5$ and (b) if $\hat{h}_D(x)\leq 0.5$, then $\hat{h}_D(x)\leq g_D(x)\leq 0.5$. One proves (a) and skips (b) because of analogy. Suppose $\hat{h}_D(x)\geq 0.5$ and $\hat{w}$ is the maximum likelihood model coefficients. This means $x\hat{w}\geq 0$. As shown in Theorem 6, for a, b found from EQS. (17) and (18) one has $a=l(\hat{w})\geq b$. Therefore $g_D(x)=(1+\exp(-a+b))^{-1}\geq 0.5$. To show $\hat{h}_D(x)\geq g_D(x)$, let $b'=l(\hat{w})-x\hat{w}$. It is easy to see that $b=\max_w(l(w)+\min(0,xw))\geq b'$. Because of $\hat{h}_D(x)=(1+\exp(-a+b'))^{-1}$, $g_D(x)=(1+\exp(-a+b))^{-1}$ and $b\geq b'$, it is concluded that $\hat{h}_D(x)\geq g_D(x)$.

Theorem 8: If $\hat{w}_a=\hat{w}_b$, then $g_D(x)=\hat{h}_D(x)$.

Proof: By Theorem 6, either $l(\hat{w}_a)=l(\hat{w})$ or $l(\hat{w}_b)=l(\hat{w})$. This means that either $\hat{w}_a$ or $\hat{w}_b$ is a maximum likelihood coefficient vector. Because $\hat{w}_a=\hat{w}_b$ one can write $\hat{w}_a=\hat{w}_b=\hat{w}$. Now $a=l(\hat{w})+\min(0,x\hat{w})$ and $b=l(\hat{w})+\min(0,-x\hat{w})$. Therefore $a-b=x\hat{w}$. Thus $g_D(x)=(1+\exp(-x\hat{w}))^{-1}$.

Note that when there is more than one model achieving the maximum likelihood, the ML method is silent on the question of which model should be used to determine the price of a gamble. In practice, to avoid such indeterminableness, a secondary and often ad hoc criterion, such as minimization of the coefficient vector's norm, is introduced to sort out among maximum likelihood models. In contrast, LGP does not have this problem because the price depends on the values of objective functions (likelihoods) rather than the locations in the coefficient space where the objective functions reach their maxima.

It is well known that MLE is asymptotically consistent and it can be shown that gamble pricing is also consistent. For convenience, one makes the technical assumption that the marginal density of X is uniform.

Theorem 9: Under standard regularity conditions, such as iid, identifiability, differentiability, open parameter space, etc., the LGP price asymptotically converges to the true value.

Proof: A sketch of the proof is provided. Denote by Z the random value obtained by joining X and Y, i.e., $Z=(X, Y)$. With the uniform marginal density assumption, one has the unconditional log likelihood $\log(Pr(z|w))=c+\log(Pr(y|x, w))$, where c is the log of the uniform density. Denote the true parameter by $w_0$. Under the standard regularity conditions the average (unconditional) log likelihood, $$c + \frac{1}{n}l(\hat{w})$$

where n is the sample size, converges to the expected log likelihood function $$E[\log Pr(Z|w)]=c+E[Pr(Y|X,w)].$$

The expected log likelihood function is maximized at the true parameter $w_0$, i.e., for any $w$, $$E[\log Pr(Y|X,w_0)] \geq E[\log Pr(Y|X,w)].$$

Suppose $xw_0 \geq 0$. Because of $\hat{w}_a = \hat{w}$ (Theorem 6) and the result that $\hat{w}$, the maximum likelihood estimate, converges to $w_0$, it holds in the limit that $\hat{w}_a = w_0$, i.e., $w_0$ is the solution of the maximization task (17). Next one has to show that, in the limit, $w_0$ is also the solution to the maximization task (18), i.e., $\hat{w}_b = w_0$:

$$l(w_0) - xw_0 \geq l(w) + \min(0, -xw)$$

for any $w$. Because $\min(0, -xw) \leq 0$, it suffices to show $l(w_0) - l(w) \geq xw_0$, or equivalently $$\frac{1}{n}(l(w_0) - l(w)) \geq \frac{1}{n} xw_0.$$

This inequality holds in the limit: RHS converges to 0 and LHS is non-negative because $$E[\log Pr(Y|X,w_0)] \geq E[\log Pr(Y|X,w)].$$

As $\hat{w}_a = \hat{w}_b = w_0$, the price given by LGP equals the true probability $g(x) = Pr(y=1|x, w_0) = (1+\exp(-xw_0))^{-1}$. The case where $xw_0 < 0.5$ is proved similarly.

Note that the properties of LGP listed in the theorems are not specific to a logistic model with a concave log likelihood function. With some minor modifications, these properties can be proven without the requirement of concavity.

Solving the Optimization Task Via Smoothing

Since for each point for which a prediction is needed, one has to solve optimization equations (17) and (18), it is useful to solve them in an efficient manner. First, one can highlight the fact that the optimization equations (17) and (18) are strictly concave problems which ensures and the existence of unique maximizers. The concavity of these objectives functions come from the fact that the function $f(y) = \min\{0, y\}$ is concave and from the well-known fact that the composition of concave functions is also concave. On the other hand, the $\min\{0, y\}$ is not differentiable which restricts or makes difficult the use of well-behaved Newton-like methods that depend on derivatives for their fast convergence rates. In order to address this, a smoothing technique will be used that will result in an objective function with more suitable properties for optimization equations (17) and (18). Since the derivative with respect to $x$ of the max function $g(x) = \max\{0, x\}$ is the step function, the differentiable function $p(x, \xi)$, the integral to the sigmoid function $(1+\exp(-\xi x))^{-1}$, is used as an smooth approximation to $g(x) = \max\{0, x\}$:

$$p(x, \xi) = x + \frac{1}{\xi} \ln(1 + \exp(-\xi x)), \xi > 0.$$

Then, given $\xi$, one has:

$$\min\{0, x\} = -\max\{0, -x\} \quad (27)$$
$$\approx -p(-x, \xi)$$
$$= x - \frac{1}{\xi} \ln(1 + \exp(\xi x))$$
$$\equiv m(x, \xi).$$

Hence instead of solving maximization EQS. (17) and (18), one solves the following smooth convex approximations:

$$\ln(\alpha^*) = \max_w \{\ln(l(w)) + m(w, x_0, \xi)\}, \quad (28)$$

$$\ln(\beta^*) = \max_w \{\ln(l(w)) + m(-w, x_0, \xi)\}. \quad (29)$$

More specifically, for the logistic regression framework under consideration, the two optimization tasks to solve are:

$$\max_w \sum_{i=1}^{n} \{(y_i - 1)(w'x_i) - \ln(1 + \exp(-w'x_i))\} + \quad (30)$$
$$(w'x_0) - \frac{1}{\xi} \ln(1 + \exp(\xi w'x_0)),$$

$$\max_w \sum_{i=1}^{n} \{(y_i - 1)(w'x_i) - \ln(1 + \exp(-w'x_i))\} - \quad (31)$$
$$(w'x_0) - \frac{1}{\xi} \ln(1 + \exp(-\xi w'x_0)),$$

which are both unconstrained concave maximization tasks for which both the gradient and the Hessian can be easily calculated. According to an embodiment of the invention, a Newton-Armijo method is used to solve EQS. (30) and (31), which provides quadratic convergence to the global solution of the approximated problem. It can be proved that the solution of this smooth approximation to the objective functions of EQS. (17) and (18) that depends on a parameter $\xi$ converges to the solution of the original equations when the parameter $\xi$ approaches infinity and it is as close as desired for appropriate large values of the smoothing parameter $\xi$.

Now suppose that $\xi = 1$ and $y_0 = 1$ in EQ. (30). It can be shown that $$\ln\left(l(w) + (w'x_0) - \frac{1}{\xi} \ln(1 + \exp(\xi w'x_0))\right) = \quad (32)$$
$$\sum_{i=0}^{n} \{(y_i - 1)(w'x_i) - \ln(1 + \exp(-w'x_i))\},$$

which is precisely the log likelihood of $w$ given that $x_0$ is a positive point in the training set. It is also trivial to show that EQ. (31) coincides with the log likelihood of $w$ given that $x_0$ is a negative point in the training set, when it is assumed $\xi = 1$ and $y_0 = 0$.

Illustration

Asymptotic properties are nice but in practice they do not provide much assurance because of the limited data availability. In this section, an LGP according to an embodiment of the invention is illustrated by an application to the space shuttle O-ring data set, illustrated in the table of FIG. 1, that became well known in the aftermath of the space shuttle Challenger catastrophe. The presidential commission created to investigate the accident concluded that the Challenger accident was caused by a combustion gas leak through a field joint in one of the booster rockets.

FIG. 2 is a graph of two curves 21, 22 computed by MLE and LGP respectively for the range of temperature from 31° F. to 81° F. These curves clearly illustrate Theorem 7. Notice that the estimates by the two methods are close in the area of data concentration but differ elsewhere. The difference is significant. For example, at 31 degrees, the prediction of MLE is 0.9996 while the prediction of LGP is 0.9551. While the MLE curve has the logistic functional form because points are calculated based on the selected MLE parameter $\hat{w}$, the LGP predictions are calculated independently and do not necessarily conform to a well-defined functional form.

Figure 3:
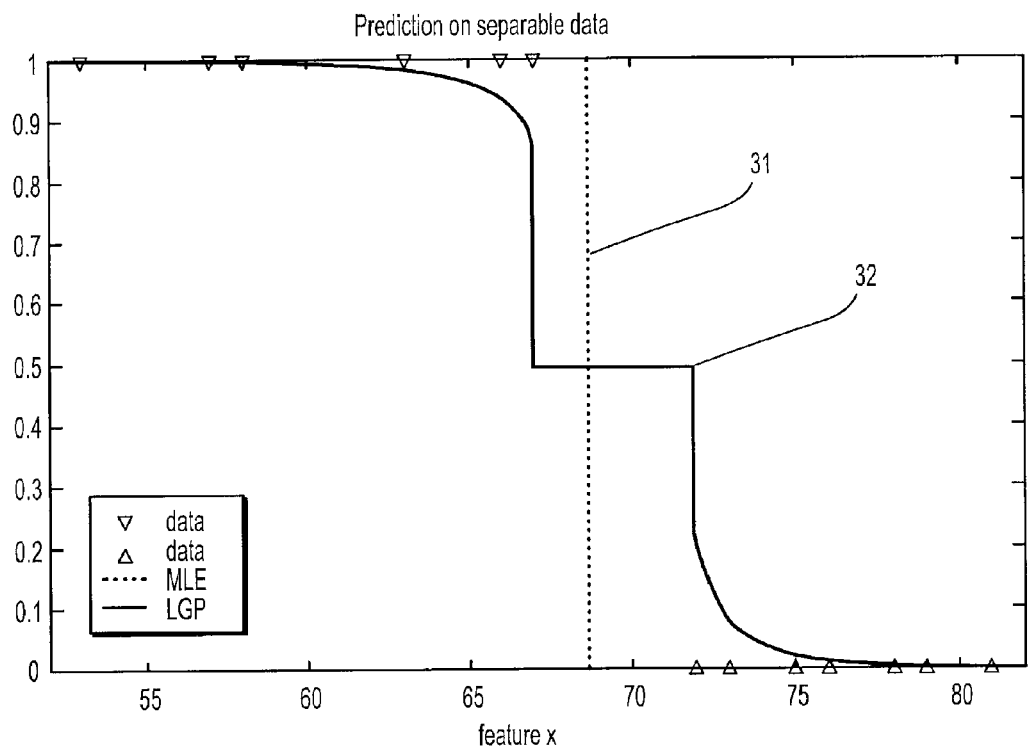
FIG. 3 illustrates results for an artificial data set, according to an embodiment of the invention.

A noticeable feature of the LGP curve is the "bump" found near the intersection with the MLE curve where LGP switches from being under the MLE curve to above the MLE curve (or vice versa). Intuitively, the bump is a reflection of the ignorance that the observed data bears on the prediction points. To illustrate that, FIG. 3 illustrates MLE 31 and LGP 32 results for an artificial data set where the maximum value when a failure is observed is 67 while the minimum value without failure is 72. In this case the data is completely separable, as the "bump" represents the state of ignorance when predictions are made for points lying between two classes. In this situation, one can argue that the data provides no clue on how O-rings would behave in the range (67, 72). For that range, LGP assigns the "ignorance" value (0.5) while MLE assigns 1 to the failure probability at values up to 68.70 and 0 at values higher than that.

This example also illustrates another property of MLE: the instability which occurs when the likelihood function is flat around its maximum. Strictly speaking, the MLE prediction 31 in FIG. 3 is not a "pure" maximum likelihood solution but a solution obtained with some regularization. Without this regularization, one can show that for any $x \in (67, 72)$ and $\epsilon > 0$, there are two models $w_1, w_2$ such that $l(w_1) > -\epsilon$, $l(w_2) > -\epsilon$, $Pr(Y=1|x, w_1) > 1-\epsilon$ and $Pr(Y=1|x, w_2) < \epsilon$. That means, one can find two models with log likelihoods arbitrarily close to 0 (the absolute upper bound) such that the predictions by those models are opposite of each other. This can be visualized by sliding the dotted line along the horizontal axis.

Understanding LGP

In this section is discussed a possible understanding of an LGP according to an embodiment of the invention in terms of virtual evidence and regularization with Fisher information.

Virtual Evidence

Consider the question of how much would one be willing to bet on Y=1 at X=x given the data $D=\{(x_i, y_i) | 1 \leq i \leq n\}$. As gamblers often find it convenient to work with odds rather than probability, the question can be rephrased into the prediction of the log odds in favor of Y=1 at point x. Notice that there is only the formula of log odds given a model $\log(Pr(Y=1|x, w)/Pr(Y=-1|x, w))=xw$. An obvious way to come up with estimate that does not depend on unknown model w is to take expectation with respect to w. So the question reduces to the estimation of E[xw].

One starts by assuming that $x=x_i$, that is, one wants to estimate the odds at a point with an observed label. Denote by $D_{-i}$ the "alternative" data obtained by flipping the label of point i i.e., $$D_{-i}=\{(x_1, y_1) \ldots (x_i, -y_i) \ldots (x_n, y_n)\}$$

The difference of log likelihoods computed on D and $D_{-i}$ is $l_D(w) - l_{D-i}(w) = y_i x_i w$. This equation implies that the log odds can be estimated through the difference of log likelihoods of D and $D_{-i}$. For simplicity assume $y_i=1$. Viewing $l_D(w)$, $l_{D-i}(w)$ and $x_i w$ as functions of w and applying expectation operator with respect to the distribution of w on both sides, one has $$E[x_i w] = E[l_D(w)] - E[l_{D-i}(w)] \quad (33)$$

Because the mean can be approximated by the mode, $E[l_D(w)]$ and $E[l_{D-i}(w)]$ are approximated by the modes mod $[l_D(w)]$ and mod $[l_{D-i}(w)]$, respectively. The bound of this approximation can be quantified. Because the log likelihood function for logistic model is concave therefore it is unimodal. Under a reasonable assumption, the probability density of w is unimodal too. In this case the distance between mean and mode is at most p3×standard deviation The mod $[l_D(w)]$ can be approximated by $\max_w l_D(w)$. Because $l_D(w)$ is a (log) likelihood function, a higher value of $l_D(w)$ indicates a higher probability (density) Pr(w). The exact relationship could be seen via Bayes theorem with the assumption of the uniform prior. The higher the density of Pr(w) translates into a higher density of $Pr(l_D(w))$. By definition $$\mathrm{mod}\,[l_D(w)] = l_D(w^*),$$

where $w^*$ is such that $Pr(l_D(w^*)) \geq Pr(l_D(w))$ for all w.

By the above approximate reasoning, $Pr(l_D(w^*)) \geq Pr(l_D(w))$ for all w holds if $l_D(w^*) \geq l_D(w)$ for all w. This means $l_D(w^*) = \max_w(l_D(w))$. One can argue similarly for mod$[l_{D-i}(w)]$. To sum up, one has $$E[l_D(w)] \approx \mathrm{mod}[l_D(w)] \approx \max_w l_D(w)$$

$$E[l_{D-i}(w)] \approx \mathrm{mod}[l_{D-i}(w)] \approx \max_w l_{D-i}(w) = \max_w (l_D(w) - xw)$$

It is reassuring that this intuitive derivation arrives at equations that are identical with the ones of an LGP approach according to an embodiment of the invention, for the special case that the "test" example is already in the training data. While it is unclear how to generalize this intuitive approach to the case of a test example that is not part of the training data, an LGP approach according to an embodiment of the invention provides a solution for the general case.

Leading-Order Approximation

This section provides another view to LGP by relating it to the typical regularization in frequentist statistics, which is based on a correction term of the maximum likelihood approach. The leading-order term that causes the regularization of the predicted price is derived. It turns out that the (observed) Fisher information plays a role. To simplify notation, assume that $x\hat{w} > 0$ (the other case $x\hat{w} \leq 0$ is similar). Recall that the price is $$P = (1 + \exp(-l(\hat{w}) + l(w^*) - xw^*))^{-1} \quad (34)$$

where $w^*$ is a solution of EQ. (25) i.e., $$w^* = \arg\max_w (l(w) - xw) \quad (35)$$

It is assumed that the value of $w^*$ is "close" to $\hat{w}$, so that the leading-order Taylor-expansion of l is accurate. This assumption can be expected to be true for large data sets as the absolute value of l(w) can be expected to grow linearly in n, while the value of xw is independent of the sample size. Hence the effect of the latter term becomes more and more negligible for large date sets, and hence $w^*$ converges asymptotically to $\hat{w}$. One can carry out a leading-order Taylor-expansion of $l(w^*)$:

$$l(w^*) = l(\hat{w}) + \frac{1}{2}(w^* - \hat{w})^T H(\hat{w})(w^* - \hat{w}) + O(|w^* - \hat{w}|^3), \quad (36)$$

where the first derivative vanishes as $\hat{w}$ is the ML solution, and H denotes the Hessian matrix of the log-likelihood evaluated at $\hat{w}$:

$$H_{j,k}(\hat{w}) = \left.\frac{\partial^2}{\partial w_j \partial w_k} l(w)\right|_{\hat{w}}.$$

Specifically, for the logistic model $$H(\hat{w}) = -\sum \frac{x_i^T x_i}{(\exp(x_i \hat{w}/2) + \exp(-x_i \hat{w}/2))^2}. \quad (37)$$

Note that $-H(\hat{w})/n$ equals the observed Fisher information matrix if no data is missing. This is discussed below. Using this leading-order approximation, one can now find the approximate solution of EQ. (35) by equating its first derivative with zero:

$$H(\hat{w})(w^* - \hat{w}) - x^T = 0 + O((w^* - \hat{w})^2). \quad (38)$$

This yields the approximate solution for $w^*$:

$$w^* = \hat{w} + H^{-1}(\hat{w}) x^T + O((w^* - \hat{w})^2) \quad (39)$$

Plugging EQS. (39), (36) into EQ. (34) yields $$p \approx (1 + \exp(-x w_R))^{-1} \quad (40)$$

where $$w_R = \hat{w} + H^{-1}(\hat{w}) x^T. \quad (41)$$

From a computational view-point, note that the values of $\hat{w}$ and $H^{-1}(\hat{w})$ need be estimated only once (during training) in this approximation, while the prediction for a new point x can then be made without solving an optimization task involving this point (in contrast to the exact solution).

The result of this approximation is that it yields the leading-order correction-term that causes the regularization of the predicted price/probability Y=1 at x compared to the ML prediction. EQ. (41) shows that the regularized parameter estimate $w_R$ differs from the ML estimate $\hat{w}$ in leading order due to the novel regularization-term:

$$\frac{1}{2} H^{-1}(\hat{w}) x^T.$$

Several comments are in order.

First, note that the correction term is not a constant but depends on the data point x whose label is to be predicted. This is an interesting difference with respect to existing model selection criteria, such as the AIC or BIC. As a consequence, the prediction is not linear in x, so that the predicted price as a function of x lies outside of the specified (linear) model class (cf. the O-ring illustration). Second, as $H^{-1}(\hat{w}) \propto 1/n$ in the asymptotic limit ($n \to \infty$), cf. EQ. (37), the regularization can be expected to decrease with growing n, and diminishes in the limit, i.e., the regularized parameter estimate then coincides with the ML estimate, as desirable (cf. also Theorem 9). Third, note that the Hessian $H^{-1}(\hat{w})$ is negative definite, as $\hat{w}$ is the ML estimate. Hence the predicted price is closer to 0.5 than the price predicted by ML, as desirable from a regularization point of view (cf. also Theorem 7). Fourth, as the Hessian $H^{-1}(\hat{w})$ describes the curvature of the log-likelihood at $\hat{w}$, the correction is larger for flatter log-likelihood surfaces. This is desirable, as a flat log-likelihood surface indicates large model uncertainty, and consequently a large uncertainty in the prediction. This can be formalized due to the fact that $-H(\hat{w})/n$ equals the observed Fisher information matrix $I(\hat{w})$ if no data is missing.

The Hessian matrix $H(\hat{w})$ is commonly identified with the observed Fisher information, $I(\hat{w})n$, where n is the number of data points. Since in the asymptotic limit ($n \to \infty$), the observed Fisher information converges to the expected Fisher information, the Cramer-Rao inequality for the unbiased estimator $\hat{w}$ provides an asymptotic lower bound of the estimator's covariance $\Sigma(\hat{w})$ in terms of the inverse Fisher information matrix, $$\Sigma(\hat{w}) \geq I^{-1}(\hat{w}) = -n \cdot H^{-1}(\hat{w}),$$

where '$\geq$' means that the difference is a positive definite matrix. Using this asymptotic bound, and provided that $\hat{w}$ is an efficient estimator, EQ. (41) suggests that $$w_R \approx \hat{w} - \frac{1}{2n} \sum (\hat{w}) x^T \quad (42)$$

for sufficiently large n. This implies that the ML estimate $\hat{w}$ is regularized by its own variance, to obtain the fair prediction for x. In the experiments reported herein, this may also explain the observed "bump" where the predicted price is close to ½.

Although this discussion has been presented in terms of the logistic model, these results hold as long as the log likelihood function l(w) is concave and the odds ratio $\Lambda = Pr(Y=1|x,w)/Pr(Y=-1|x,w)$ is a linear function of xw which is true for the family of the generalized linear models.

Simulation Study

A limitation of relying on real data to study the properties of a method is the lack of replicability. This issue can be addressed by a simulation study. Here, an LGP method according to an embodiment of the invention will be contrasted against MLE on data simulated by the logistic model. The basic step is as follows. First, generate training data D from a known coefficient vector $w_0$ and then compare the predictions based on D for the testing data T by LGP and ML methods against the true response probabilities computed from $w_0$ and T. A measure of accuracy that can be used is the mean square error, which is the average of squared distance between predictions and true response probabilities. Another accuracy measure is the Kullback-Leibler (KL) divergence that can be applied for distributions on $T \times \{1,-1\}$ assuming a uniform marginal on T.

1. Given (1) a coefficient vector $w_0$, (2) a sample on the feature domain $S = \{x_i | 1 \leq i \leq n\}$ for training and (3) another sample $T = \{x_j | 1 \leq j \leq m\}$ for testing.

2. Compute true response probabilities for $x_i \in S$:

$$p_i = (1 + \exp(-x_i w_0))^{-1}.$$

Generate response labels $y_i$ by a Bernoulli generator $Pr(y_i=1) = p_i$ and $Pr(y_i=-1) = 1 - p_i$. Join $x_i$ and $y_i$ to form training data $D = \{(x_i, y_i)\}$ 3. Compute true response probabilities R for $x_j \in T$: $R = (1 + \exp(-T w_0))^{-1}$. Compute predictions based on D for T by LGP: $L = g_D(T)$ and by MLE: $M = \hat{h}_D(T)$.

4. Compute mean square errors $$mse_{LGP} = \frac{1}{m} \sum_j (L_j - R_j)^2,$$

$$mse_{MLE} = \frac{1}{m} \sum_j (M_j - R_j)^2.$$

5. Compute $KL(Pr_R || Pr_L)$ and $KL(Pr_R || Pr_M)$ where $Pr_R$, $Pr_M$, $Pr_L$ are distributions on $T \times \{1,-1\}$ computed from conditional $Pr(Y=1|w_0, x_j)$ and uniform marginal $Pr(x_j) = 1/m$. For example $$PrR((x_j, 1)) = R_j/m; PrR((x_j, -1)) = (1 - R_j)/m.$$

For a configuration of dimensionality d of X (excluding the intercept) and training sample size n, one generates v coefficient vectors and for each of those generate s training samples and a testing sample of size m. Each mse value reported is the average of v×s×m predictions. The goal is to isolate the effect of prediction methods from any possible effect of coefficients, testing and training values by averaging the latter out.

Figure 4:
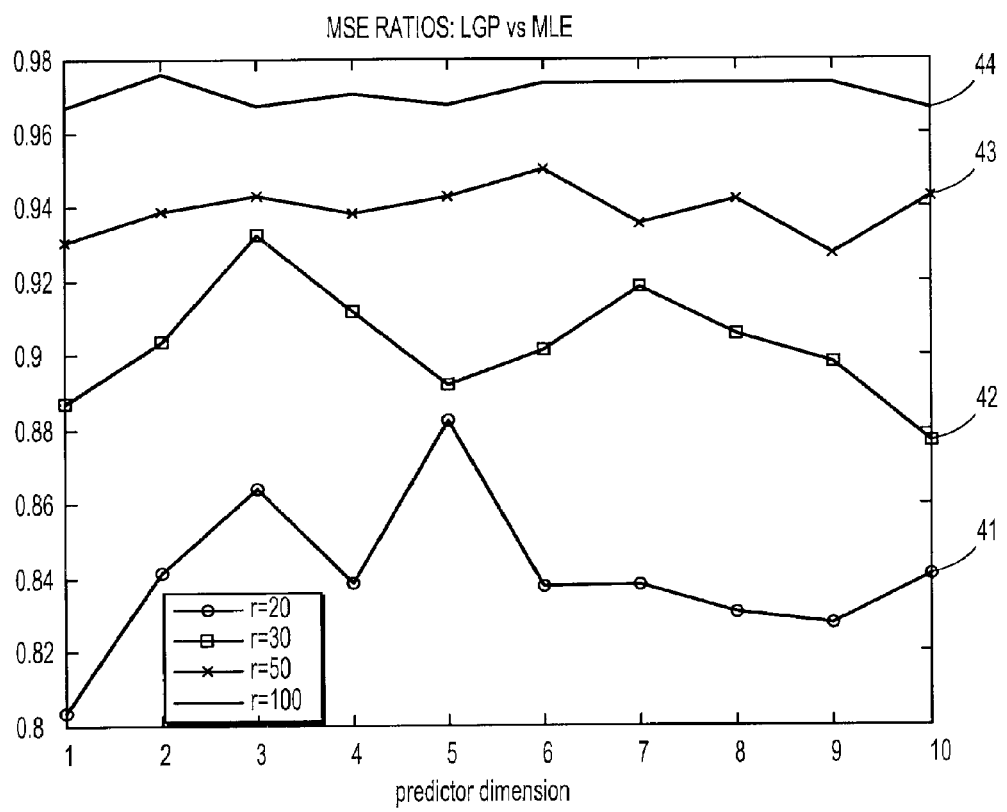
FIG. 4 is a plot that connects mse data points corresponding the same ratio of training data size over dimensionality, according to an embodiment of the invention.
Figure 5:
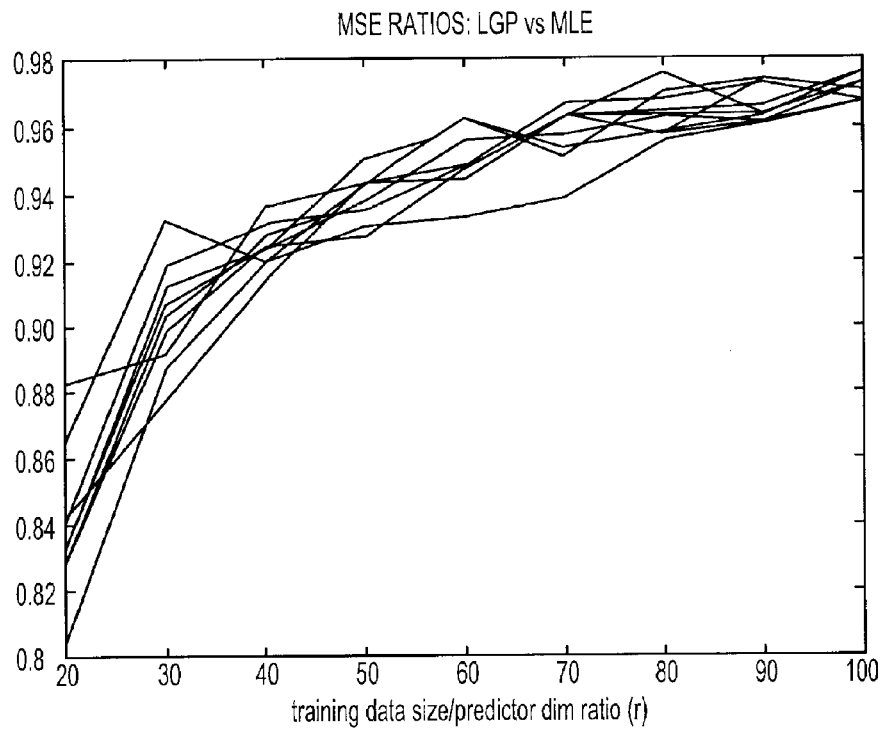
FIG. 5 is a plot that connects mse data points of the same dimensionality d, according to an embodiment of the invention.

In a first experiment, the dimensionality (d) varied from 1 to 10 and training data size over dimension ratio (r) varied from 20 to 100 with step 10. The sample size is n=r×d, with v=10, s=100 and m=100. Each number is the average of 105 squared errors. FIGS. 4 and 5 are two views to the mse data. FIG. 4 connects mse data points corresponding the same ratio of training data size over dimensionality. Plots 41, 42, 43, and 44 are presented for dimension ratio (r) values of 20, 30, 50, and 100, respectively. The mse ratio remains insensitive to predictor's dimensionality (d) given a constant ratio of training data size over dimensionality (r). It shows that mse ratio depends on r but not on d. FIG. 5 connects mse data points of the same dimensionality d. For the purpose of clarity, the individual plots are not referenced. The plots show the trend of mse ratio in response to data availability. When training data is scarce, the mse ratio is in the 80%-90% range. For each value of dimensionality, as the training data size increases, the mse ratio increases and approaches 96%-98%.

Figure 6:
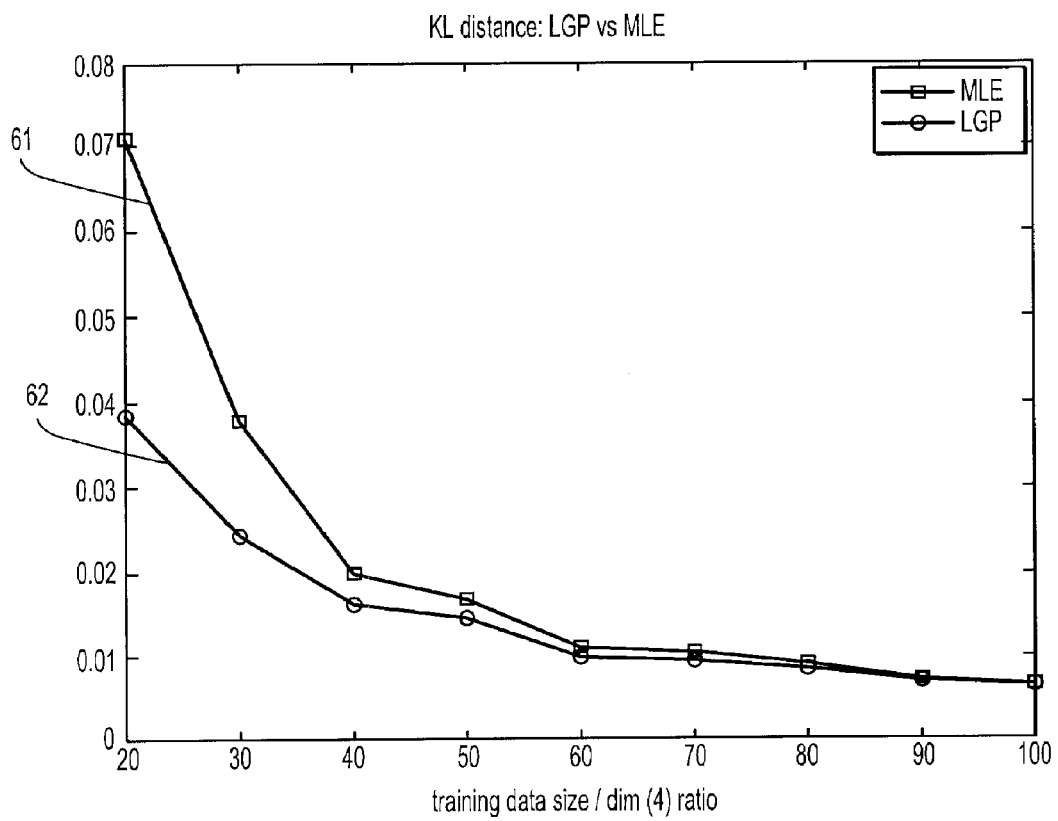
FIG. 6 is a graph of the average of KL distances computed for 1000 predicted distributions, according to an embodiment of the invention.

In a second experiment, with fixed d=4, the training size was varied from 80 to 400 with step 40, with v=10, s=100 and m=100. But instead of mse, KL distances were compared. FIG. 6 presents KL divergence results for both MLE 61 and LGP 62. Thus, each number shown in FIG. 6 is the average of KL distances computed for 1000 predicted distributions. The results in FIG. 6 indicate that the KL distance of an LGP according to an embodiment of the invention is less than one by MLE. The difference is larger when the training data is rare. For other values of d, similar patterns were observed.

Alternative Formulation of Likelihood Gamble Pricing for Binary Classification

An LGP approach according to an embodiment of the invention will now be described from a statistical perspective. The results presented above will now briefly reviewed using a statistical notation rather than a decision theoretic notation. Given training data $D=\{(y_i, x_i, w_i)\}$, $i=1, \ldots, N$ with N examples, where $x_i$ are the input vectors, $y_i \in \{0,1\}$ is the label, and $w_i \in R$ is the weight of example i for training the classifier, (omitting $w_i$ implies $w_i=1$), an objective is, given a new example $x_0$, to predict the probability $y_0^f \in [0,1]$ that its label equals 1:

$$y_0^f = p^f(y_0=1|x_0).$$

For convenience, the label $y \in \{0,1\}$ and the probability $p(y=1|x) \in \{0,1\}$ will be used interchangeably, as the latter may be considered the continuous version of the former.

In an LGP approach according to an embodiment of the invention, as outlined above, this prediction task is solved by determining a fair price of the gamble, which corresponds to the probability $y_0^f$ in a statistical perspective.

In the LGP approach, one first chooses a model class to be used, with model parameter-vector $\beta$. Then, LGP directly yields the estimate $y_0^f$ for a given example $x_0$. It does not yield an estimate of the parameter-vector $\beta$. The estimate $y_0^f$ follows directly from the 'fair' value of the likelihood ratio $\Lambda^f$. The link between $y_0^f$ and $\Lambda^f$ depends on the model class used. For example, for logistic regression, $\text{logit}(y_0^f)=\log \Lambda^f$ with the logit function as defined above. For simplicity, it can be assumed that the so-called ambiguity adverse degree is zero.

In an LGP approach, the 'fair' value of the likelihood-ratio is calculated as follows:

$$\Lambda^f = \tilde{L}_1^* / \tilde{L}_0^*, \quad (43)$$

with $$\tilde{L}_1^* = \max_\beta \lfloor \tilde{L}(\beta, D) \cdot \tilde{L}(\beta | y_\diamond = 1, x_\diamond) \rfloor, \quad (44)$$

$$\tilde{L}_0^* = \max_\beta \lfloor \tilde{L}(\beta, D) \cdot \tilde{L}(\beta | y_\diamond = 0, x_\diamond) \rfloor,$$

where the $\tilde{L}$'s denote normalized likelihoods, i.e., $\max \tilde{L}=1$. Note that likelihoods that differ by a constant normalization factor are equivalent concerning the information about the data. The (technical) reason for this normalization in the LGP approach is that is ensures a one-to-one mapping between the space of likelihood ratios $\Lambda$ and the pair of normalized likelihoods ($\tilde{L}_1^*, \tilde{L}_0^*$). In EQ. (44), the normalized likelihoods in light of example $x_0$ are given by:

$$\tilde{L}(\beta|y_0=1,x_0)=\min\{1,\Lambda(\beta|x_0)\},$$

$$\tilde{L}(\beta|y_0=0,x_0)=\min\{1,1/\Lambda(\beta|x_0)\}, \quad (45)$$

which is the inverse of the mapping $\Lambda(\beta|x_0)=\tilde{L}(\beta|y_0=1,x_0)/\tilde{L}(\beta|y_0=0,x_0)$.

In an LGP approach according to an embodiment of the invention, it is desired to solve the joint optimization task in EQ. (44) as to predict $y_0^f$ for the example $x_0$ in light of the training data D.

Simplifying the Optimization Task

Solving the optimization tasks of EQ. (44) is computationally challenging as the min-function is not differentiable at zero. Next are derived several properties of the solution, which leads to an equivalent pair of equations that is computationally easier to solve.

For convenience, the log-space is used with the normalized log-likelihood $\tilde{l}=\log \tilde{L}$ and the log-likelihood ratio $\lambda=\log \Lambda$. The optimization task then becomes, combining EQS. (44) and (45):

$$\tilde{l}_1^* = \max_\beta \lfloor \tilde{l}(\beta | D) + \min\{0, \lambda(\beta | x_\diamond)\} \rfloor, \quad (46)$$

$$\tilde{l}_0^* = \max_\beta [\tilde{l}(\beta | D) + \min\{0, -\lambda(\beta | x_\diamond)\}],$$

or equivalently $$\beta_1^* = \underset{\beta}{\operatorname{argmax}} [\tilde{l}(\beta | D) + \min\{0, \lambda(\beta | x_\diamond)\}], \quad (47)$$

$$\beta_0^* = \underset{\beta}{\operatorname{argmax}} [\tilde{l}(\beta | D) + \min\{0, -\lambda(\beta | x_\diamond)\}].$$

The following statements are assumed

1. The log likelihood $\tilde{l}(\beta|D)$ is a strictly concave function of $\beta$.

2. The log-likelihood $\tilde{l}$ is a function of the scalar $x\beta$, and the log-likelihood-ratio $\lambda(\beta|x)$ is an affine function of the scalar $x\beta$.

Note that these assumptions hold for several model classes, including generalized linear models.

The optimization task in EQ. (47) is equivalent to the following one, which does not involve the (non-differentiable) min-function and hence is more amenable to numerical optimization methods.

Proposition: Under the assumptions (1) and (2), the optimization task in EQ. (47) is equivalent to the pair $$\hat{\beta} = \underset{\beta}{\operatorname{argmax}}\, l(\beta | D), \quad (48)$$

$$\beta^* = \underset{\beta}{\operatorname{argmax}}[l(\beta | D) - \operatorname{sign}(\lambda(\hat{\beta} | x_\diamond))\lambda(\beta | x_\diamond)]. \quad (49)$$

The mapping between $\beta^*_0, \beta^*_1$ and $\hat{\beta}, \beta^*$ is as follows:

if $\operatorname{sign}(\lambda(\hat{\beta}|x_0)) > 0$ then $\beta^*_1 = \hat{\beta}$ and $\beta^*_0 = \beta^*$ else $\beta^*_1 = \beta^*$ and $\beta^*_0 = \hat{\beta}$.

Note that $\operatorname{sign}(\lambda(\hat{\beta}|x_0))$ is a constant for fixed D in EQ. (49). This is because $\hat{\beta}$ is determined by EQ. (48), and thus is a constant when optimizing EQ. (49). Moreover, note that one has witched from normalized log-likelihoods to the standard (unnormalized) log-likelihoods: in the normalization condition $\tilde{l} = l - \hat{l}$, the maximum likelihood $\hat{l} = l(\hat{\beta}|D)$ serves as the normalization constant; as $\hat{l}$ is a constant when optimizing over $\beta$, it hence can be ignored.

Proof: As $\lambda(\beta|x_0)$ is affine (Assumption 2), the function $\min\{\min\{0, \lambda(\beta|x_0)\}, \min\{0, -\lambda(\beta|x_0)\}\} = -|\lambda(\beta|x_0)|$ is concave in $\beta$. As the log-likelihood is strictly concave (Assumption 1), the optimization task $$\beta^* = \underset{\beta}{\operatorname{argmax}}[\tilde{l}(\beta | D) - |\lambda[\beta | x_\diamond]|] \quad (50)$$

has to be strictly concave. Hence it has exactly one solution $\beta^*$.

Next one proves that $\operatorname{sign}(\lambda(\beta^*_1|x_0)) = \operatorname{sign}(\lambda(\beta^*_0|x_0))$ by contradiction: if $\operatorname{sign}(\lambda(\beta^*_1|x_0)) \neq \operatorname{sign}(\lambda(\beta^*_0|x_0))$ in EQS. (47), then this would erroneously imply that EQ. (50) has two different solutions. This implies that $\min\{0, \lambda(\beta^*_1|x_0)\} = 0$ or $\min\{0, -\lambda(\beta^*_0|x_0)\} = 0$, and hence the solution to one of the optimization tasks in EQ. (47) is the maximum likelihood estimate $\hat{\beta} = \arg \max_\beta \tilde{l}(\beta|D)$. Finally, this shows that $\operatorname{sign}(\lambda(\hat{\beta}|x_0)) = \operatorname{sign}(\lambda(\beta^*_1|x_0)) = \operatorname{sign}(\lambda(\beta^*_0|x_0))$ so that, in EQ. (50), $|\lambda(\beta^*|x_0)| = \operatorname{sign}(\lambda(\hat{\beta}|x_0))\lambda(\beta^*|x_0)$, which completes this sketch of the proof.

Combining the Proposition with EQ. (43), one can now obtain for the 'fair' value of the log likelihood ratio $\lambda^f = \log \Lambda^f$:

$$\lambda^f = \lambda(\beta^*|x_0) + \operatorname{sign}(\lambda(\hat{\beta}|x_0))\{l(\hat{\beta}|D) - l(\beta^*|D)\}. \quad (51)$$

This shows that, compared to the maximum likelihood solution $\lambda(\hat{\beta}|x_0)$, the LGP approach achieves regularization of the predicted 'fair' log-likelihood-ratio and hence of the predicted probability $y_0^f$ in a novel way: the degree of regularization depends not only on the training data D but also on the example $x_0$ to be classified. Moreover, another interesting property is that regularization in the LGP approach does not have a free parameter that needs to be tuned. Moreover, with Assumption 2, the optimization tasks (EQS. 48 and 49) and hence the predicted $\lambda^f$ and $y_0^f$ are invariant under affine transformations of the input space x. While scale-invariance of the regularization mechanism is a useful property, note that many popular approaches do not posses this property, e.g., like the hinge loss used in SVMs.

Approximation by Likelihood

In this section is derived a simple leading-order approximation to the second equation derived in the previous section, EQ. (49) such that it becomes a standard maximum likelihood task as well. This approximation enables to predict the fair price or probability of the label in an LGP approach according to an embodiment of the invention by solving two standard maximum likelihood tasks. Moreover, it turns out that this approximation also yields interesting insights into the underlying regularization-mechanism.

In detail, assume that the second term in EQ. (49), which is based on the single example $x_0$ to be classified, can be considered as a small disturbance to the first term, which is the log likelihood of the entire training data D, containing $N \gg 1$ examples. In other words, assume that $\beta^*$ is close to $\hat{\beta}$, which will be specified more rigorously in EQ. (54). One approximates the second term in EQ. (49) by the log likelihood $l(\beta|(y_0, x_0, w_0))$ in light of the new example $x_0$ to be classified. This results in the constraint $$-\operatorname{sign}(\lambda(\hat{\beta}|x_0))\lambda(\beta^*|x_0) = l(\beta^*|(y_0, x_0, w_0)) \quad (52)$$

where the label $y_0$ and the weight $w_0$ of the example $x_0$ are unknown for the moment. Determining their approximate values based on this constraint is the goal of the remainder of this section. One expands EQ. (52) about $\hat{\beta}$ to obtain:

$$c_1(\hat{\beta}) - x_\diamond(\beta - \hat{\beta})\operatorname{sign}(\lambda(\hat{\beta}|x_\diamond)) \frac{\partial}{\partial(x_\diamond\beta)}\lambda(\beta|x_\diamond)\bigg|_{\beta=\hat{\beta}} \quad (53)$$

$$= c_2(\hat{\beta}) - x_\diamond(\beta - \hat{\beta}) \frac{\partial}{\partial(x_\diamond\beta)} l(\beta|(y_\diamond, x_\diamond, w_\diamond))\bigg|_{\beta=\hat{\beta}} + O((x_\diamond(\beta - \hat{\beta}))^2). \quad (54)$$

where $c_1(\hat{\beta})$ and $c_2(\hat{\beta})$ are the zeroth order terms of the Taylor expansion about $\hat{\beta}$. These terms are constant when optimizing over $\beta$, and thus can be ignored in the optimization task.

Given that $l(\hat{\beta}|(y_0, x_0, w_0)) = w_0 \cdot l(\hat{\beta}|(y_0, x_0, 1))$, EQ. (54) can now be solved for the weight $w_0$. Retaining only the relevant terms for the optimization task, one obtains $$w_\diamond = -\frac{\frac{\partial}{\partial(x_\diamond\beta)}|\lambda(\beta|x_\diamond)|}{\frac{\partial}{\partial(x_\diamond\beta)} l(\beta|(y_\diamond, x_\diamond, 1))}\bigg|_{\beta=\hat{\beta}} + O((x_\diamond(\beta - \hat{\beta}))^2). \quad (55)$$

This explicit equation enables one to calculate the weight $w_0$ to be used when optimizing the approximation (see EQ. (56), below). Note that $w_0$ depends on the (unknown) label $y_0$ of the example $x_0$ to be classified. This is expected, as both $w_0$ and $y_0$ were introduced into the approximation (see right-hand side of EQ. (52)), while the original task (see left-hand side of EQ. (52)) is independent of both variables. EQ. (52) implies that the weight $w_0$ compensates for the unknown label $y_0$ such that the final result (i.e. $\beta^*$ in EQ. (56)) is independent of $y_0$ in this approximation. Note that the value of $y_0$ should be chosen before solving the optimization task of EQ. (56). Hence there should be a mechanism, namely the weight $w_0$, to compensate for a possibly suboptimal choice for $y_0$.

Even though this shows that the choice of $y_0$ does not have much impact on the result, remember that the weight $w_0$ does not compensate for changes in $y_0$ in second or higher orders of the Taylor expansion of $l(\hat{\beta}|(y_0, x_0, w_0))$. Even though these approximation errors are typically negligible, they may become noticeable when a 'bad' choice was made for $y_0$, which may also entail numerical instabilities. To avoid such 'bad' choices for $y_0$, one can either choose value $y_0$ as an appropriate function of example $x_0$, or simply stick to a default value of $y_0$ independent of the example $x_0$. It was found by experiment that the latter approach is sufficient to avoid numerical problems when one chooses $y_0 = 0.5$ for any $x_0$, which is neutral regarding the labels 0 and 1, and then calculates the weight $w_0$ according to EQ. (55).

Having derived the leading-order approximation to the second term in EQ. (49), one can now obtain the following approximation, inserting EQ. (52) into EQ. (49):

$$\beta^* = \underset{\beta}{\mathrm{argmax}}\, l(\beta|D) - \mathrm{sign}(\lambda(\hat{\beta}|x_\diamond))\lambda(\beta|x_\diamond) \quad (56)$$

$$= \underset{\beta}{\mathrm{argmax}}\, l(\beta|D) + l(\beta|(y_\diamond, x_\diamond, w_\diamond)) + O((x(\beta - \hat{\beta}))^2)$$

$$= \underset{\beta}{\mathrm{argmax}}\, l(\beta|D \cup \{(y_\diamond, x_\diamond, w_\diamond)\}) + O((x(\beta - \hat{\beta}))^2).$$

This approximation is a standard maximum likelihood task, and hence can be solved with any standard software package. Interestingly, the example $x_0$ to be classified, with label $y_0$ and weight $w_0$ as derived above, serves as an additional data point besides the training data D. Apart from that, the maximum likelihood prediction for $y_0^f$ is obtained from EQ. (56) if one sets $w_0$=0.

Figure 7:
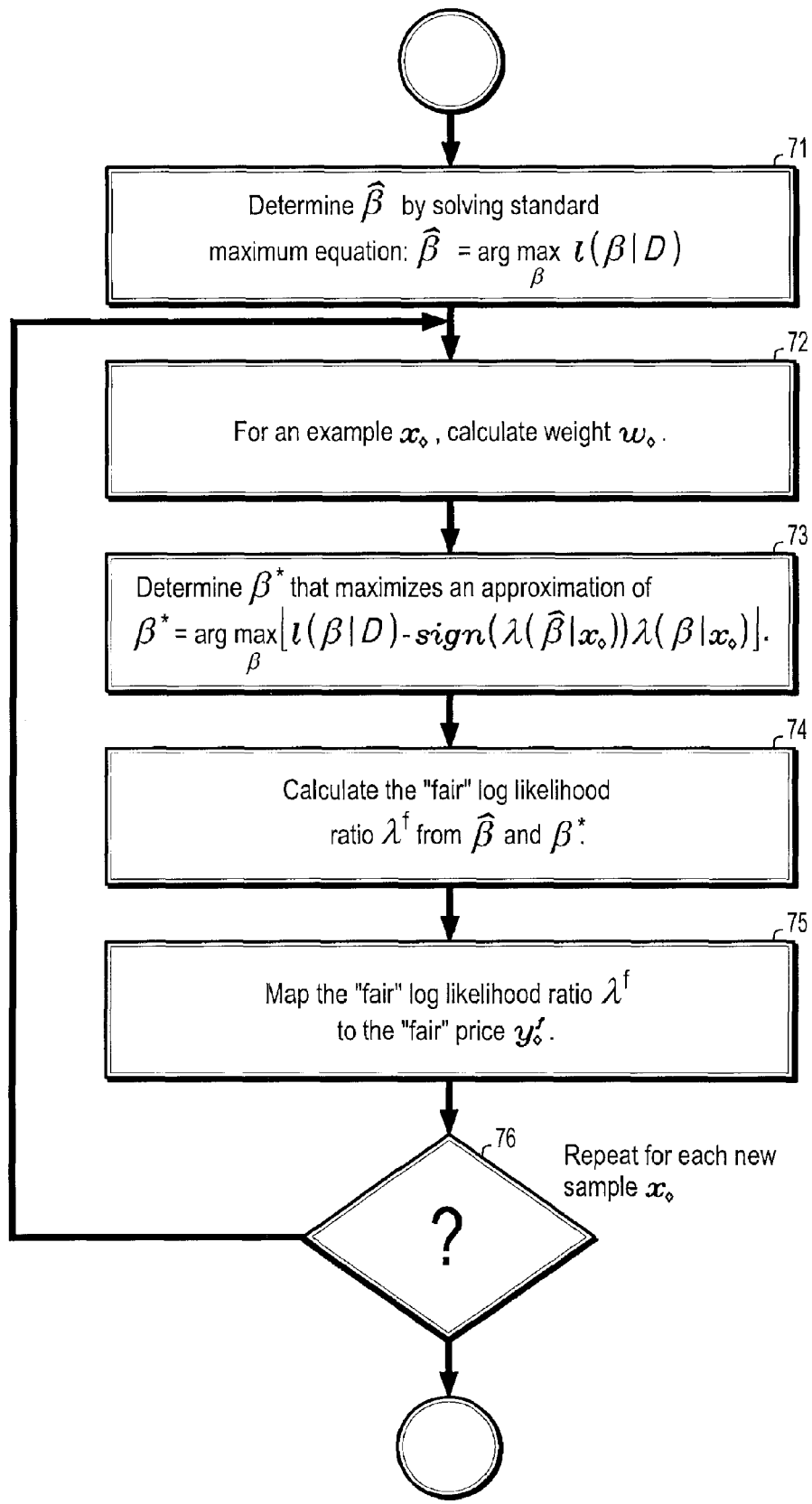
FIG. 7 is a flowchart of a procedure for a likelihood gamble pricing approach to binary classification according to an embodiment of the invention.

Thus, given a model class, training data D and an example $x_0$ whose label-probability $y_0^f$ is to be predicted, the derivation above can be summarized as illustrated in the flowchart of FIG. 7. Referring now to the figure, a derivation is as follows.

1. At step 71, determine $\hat{\beta}$ by solving standard maximum likelihood task of EQ. (48), $$\hat{\beta} = \underset{\beta}{\mathrm{argmax}}\, l(\beta|D).$$

2. At step 72, for an example $x_0$, calculate weight $w_0$ from EQ. (55):

$$w_\diamond = -\frac{\frac{\partial}{\partial(x_\diamond\beta)}|\lambda(\beta|x_\diamond)|}{\frac{\partial}{\partial(x_\diamond\beta)}l(\beta|(y_\diamond, x_\diamond, 1))}\bigg|_{\beta=\hat{\beta}}.$$

3. At step 73, determine $\beta^*$ by solving the maximum likelihood in EQ. (56):

$$\beta^* = \underset{\beta}{\mathrm{argmax}}\, l(\beta|D \cup \{(y_\diamond, x_\diamond, w_\diamond)\})\ldots$$

4. Now that $\hat{\beta}$ and $\beta^*$ are determined, the 'fair' log likelihood ratio $\lambda^f$ can be calculated from EQ. (51) at step 74: $\lambda^f = \lambda(\beta^*|x_0) + \mathrm{sign}(\lambda(\hat{\beta}|x_0))\{l(\hat{\beta}|D) - l(\beta^*|D)\}$.

5. Finally, at step 75, $\lambda^f$ can be mapped to the 'fair' price $y_0^f$. This mapping depends on the model class used (see next section for examples).

Note that step 1 needs to be computed only once, while steps 2 through 5 are looped from step 76 for every new example $x_0$ to be classified. Note that $\hat{\beta}$ can serve as an initialization for optimizing $\beta^*$.

If $\beta^*$ is not close to $\hat{\beta}$, then the accuracy of the linear approximation can be improved by iterating steps 2 and 3 until convergence. In this case, use in step 2 the value $\beta^*$ from the previous iteration in place for $\hat{\beta}$.

There are variants of this approach. One variant according to an embodiment of the invention is obtained by choosing an approximation for the weight $w_0$ that is different from the one in step 2. The simplest possible one is $w_0$=2 for any example $x_0$ in step 2 for the logistic regression model. Equivalently to choosing $w_0$=2, one can also insert 2 data points, each with weight 1, at step 4. For example, $$\beta^* = \underset{\beta}{\mathrm{argmax}}\, l(\beta|D \cup \{(1, x_\diamond, 1), (0, x_\diamond, 1)\}). \quad (57)$$

Alternatively, instead of inserting the two data points into the 'augmented' data, one can insert one data point into the one data set in step 1, and the other data point in to the other data set in step 3. This replaces the steps 71, 72, 73 and 74 of FIG. 7 by the following 3 steps:

1. $l_1 = \underset{\beta}{\max}\, l(\beta|D \cup \{(1, x_\diamond, 1)\}).$ (58)

2. $l_0 = \underset{\beta}{\max}\, l(\beta|D \cup \{(0, x_\diamond, 0)\}).$ (59)

3. $\lambda^f = l_1 - l_0.$ (60)

Models

Various models can be used with an LGP approach according to an embodiment of the invention, including generalized linear models. Herein below are presented equations for two exemplary, non-limiting models, the logistic regression model and the Gaussian classifier model, which follow immediately from the general equations derived above.

Logistic Regression Model

For the logistic regression model, the probability y is linked to the log-likelihood ratio $\lambda$ via the logistic function, which would be used in step 5 above:

$$p(y = 1|x, \beta) = \frac{1}{1 + \exp(-\lambda(\beta|x))} \quad (61)$$

where $\lambda(\beta|x) = x\beta$ is linear (cf. Assumption 2). In the light of data D, the log-likelihood of $\beta$, to be used in step 71, reads $$l(\beta|D) = \sum_{i=1}^{N} w_i\{(y_i - 1)x_i\beta - \log(1 + \exp(-x_i\beta))\}. \quad (62)$$

Standard gradient-based methods can be used to determine the maximum likelihood solutions $\hat{\beta}$ and $\beta^*$ in steps 1 and 3 above.

To determine $\hat{\beta}$ and $\beta^*$; the optimization task summarized above can be solved. The equation for $\beta^*$ at step 73 would use the same $l(\beta|D)$ as that used for $\hat{\beta}$ in step 71, $$l(\beta|D) = \sum_{i=1}^{N} w_i\{(y_i - 1)x_i\beta - \log(1 + \exp(-x_i\beta))\}.$$

The interesting part is to calculate the weight $w_0$ in EQ. (55), used in step 72 above, for the logistic regression model:

$$w_\diamond = \frac{-\text{sign}(x_\diamond\hat{\beta})}{y_\diamond - 1 + \dfrac{1}{1 + \exp(x_\diamond\hat{\beta})}},$$

which can be easily evaluated. Interestingly, for the choice $y_0=0.5$, one has $$w_0 \to 2 \text{ as } |x_0\hat{\beta}| \to \infty,$$

i.e., in both the extreme cases where the predicted price of $x_0$ is close to 0 or close to 1, the new example $x_0$ is assigned the weight 2, interestingly not 1. Hence, this example is treated like two examples with label $y_0=0.5$, or equivalently like one with label 1 and second one with label 0. In between these two extremes, the weight $w_0$ increases continuously as $|x_0\hat{\beta}|$ decreases, and diverges at the origin:

$$w_0 \to \infty \text{ as } x_0\hat{\beta} \to 0.$$

Thus, according to an embodiment of the invention, this behavior of the weight suggests an additional approximation: assign $w_0=2$ for all values of $x_0\hat{\beta}$, as suggested by the asymptotic limit above. This results in a particularly simple approach: $\beta^*$ is the maximum likelihood solution in light of the data $D \cup \{(1,x_0,1),(0,x_0,1)\}$. As the weight $w_0$ deviates from 2 for examples close to the decision boundary, one expects the approximation error of this additional simplification to be concentrated around $y_0^f=0.5$.

Figure 8:
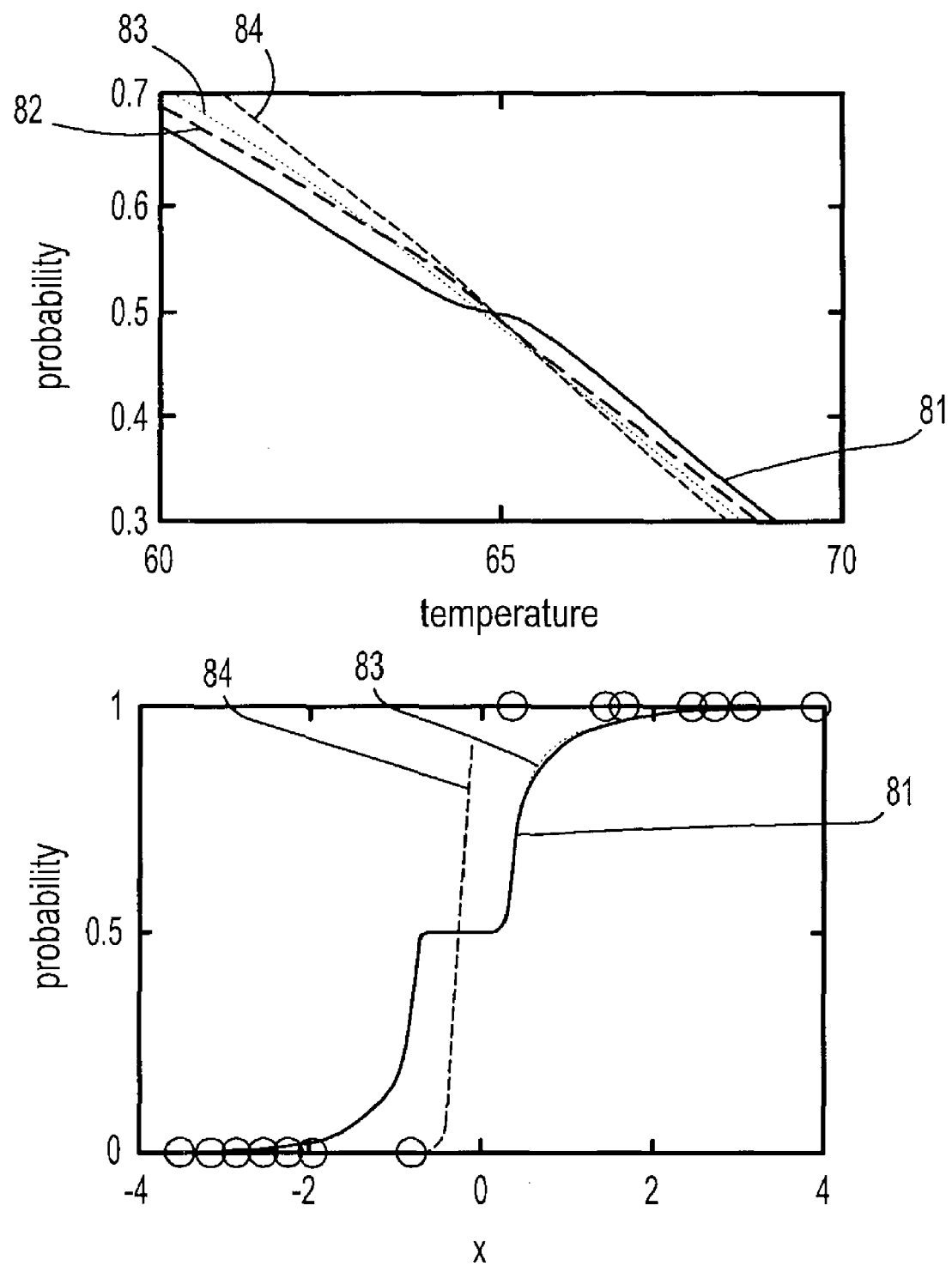
FIG. 8 illustrates the properties of an LGP approach according to an embodiment of the invention and of the approximations to space shuttle o-ring data.

This is indeed observed experimentally. FIG. 8 illustrates the properties of an LGP approach according to an embodiment of the invention and of the approximations to the Challenger o-ring data. This data was modified slightly as to obtain a binary label, and the resulting data points are plotted as circles in the figure. FIG. 8, bottom, displays the results for separable data, where each class is represented by 10 random samples from a normal distribution. The figure plots results for an LGP approach 81, an LGP approach with fixed weights $w_0$ 82, the MAP ratio 83, and the maximum likelihood 84. The constant weight $w_0=2$ results in the disappearance of the 'bump' around $y_0^f=0.5$, as shown in the top plot of FIG. 8. This 'bump' is a characteristic of an LGP approach according to an embodiment of the invention, as it appears in the exact solution as well as in the numerically efficient approximation calculating the weight according to EQ. (55). The 'bump' reflects a large degree of uncertainty present close to the decision boundary. This is especially apparent from the bottom plot of FIG. 8, which shows that, in the case of separable data, an LGP according to an embodiment of the invention predicts $y_0^f=0.5$ in between the two classes, which means that both labels have the same probability. Note that an LGP approach according to an embodiment of the invention with fixed weight $w_0=2$ as well as the maximum-a-posteriori ratio are essentially the same 'bump' for this separable example, the reason being that the weight $w_0$ is notably different from 2 only in a very small region that is considerably smaller than the width of the 'bump', and hence has no noticeable effect here. This 'bump' is a desirable behavior, as it truly reflects the uncertainty. Apart from that, note that the prediction of an LGP approach according to an embodiment of the invention is always less extreme (i.e., closer to 0.5) than the prediction of the (unregularized) maximum likelihood approach. This suggests that an LGP approach according to an embodiment of the invention provides a prediction that is well-regularized and accounts for the uncertainty in the data.

Note that setting $w_0=2$ is exemplary and non-limiting, and other approximations for $w_0$ are within the scope of other embodiments of the invention.

The fair log likelihood ratio for the logistic regression model, used in step 74 of FIG. 7, is provided (cf. EQ. 51):

$$\lambda^f = x_0\beta^* + \text{sign}(x_0\hat{\beta})[l(\hat{\beta}|D) - l(\beta^*|D)]. \qquad (63)$$

Finally, the fair price for the logistic regression model is $$y_\diamond^f = \frac{1}{1 + \exp(-\lambda^f)}.$$

Gaussian Classifier Model

Assume there are two clusters with a Gaussian distribution for either class, $N(0,\sigma^2)$ and $N(1,\sigma^2)$, the log-likelihood of the model in light of the data D, used in steps 71 and 73 for calculating $\hat{\beta}$ and $\beta^*$, respectively, is $$l(\beta|D) = -\sum_{i=1}^{N} w_i(x_i\beta - y_i)^2/\sigma^2. \qquad (64)$$

It can be easily seen that $\sigma$ cancels out for the prediction of the fair price, and hence may be omitted.

The log likelihood ratio concerning the new example, used in step 74, is $$\lambda(\beta|x) = \log\frac{p(y=1|x,\beta)}{p(y=0|x,\beta)} = (2x\beta - 1)/\sigma^2, \qquad (65)$$

and the predicted label is given by $y(x,\beta)=x\beta=1+\lambda(\beta|x)\sigma^2/2$.

The value of the weight $w_0$ of the new example, used in step 72, reads (see EQ. (55)):

$$w_\diamond = \frac{-\text{sign}(2x_\diamond\hat{\beta} - 1)}{x_\diamond\hat{\beta} - y_\diamond}.$$

Note that this weight is negative, diverges to minus infinity at $x_0\hat{\beta}=0.5$, assuming $y_0=0.5$ as before, and converges to zero in the limit $|x_0\hat{\beta}| \to \infty$. The latter fact does not mean, however, that the example's effect on the regularized prediction becomes negligible due to the vanishing weight: it is offset by the contribution $(x_0\hat{\beta}-y_0)^2$ to the likelihood.

Finally, with the solutions of the two optimization tasks, the fair prediction of the label is (see EQS. (61) and (51)):

$$y_\diamond^f = 1 + \lambda^f\sigma^2/2 \qquad (66)$$

$$= x_\diamond\beta^* + \frac{\text{sign}(2x_\diamond\hat{\beta} - 1)}{2}(l(\hat{\beta}|D) - l(\beta^*|D)).$$

Experimental results for the Gaussian model show the same general properties as the results for the logistic regression model.

Comparison to Bayesian Statistics

If Bayesian hypothesis testing is modified in two ways, as suggested by an LGP approach according to an embodiment of the invention, then similar results concerning the prediction of the probability $y_0^f$ of the unlabeled example $x_0$ can be achieved.

In Bayesian statistics, hypothesis testing is typically done by means of the Bayes factor, which quantifies the evidence in favor of a hypothesis $H_1$ vs. a competing hypothesis $H_0$. The training data is a set of labeled data points $D=\{(y_i,x_i)|1\leq i\leq n\}$ where $y_i\in\{0,1\}$ are labels for data points $x_i$ which are vectors in a multidimensional real space called feature values. The Bayes factor is the ratio of the (marginal) likelihoods of the two hypotheses in light of the data D. If one wishes to incorporate the prior ratio of the two hypotheses, one arrives at the posterior ratio.

Prediction of the binary label $y_0$ of a new example $x_0$ may be considered as distinguishing between two alternative hypotheses, namely $y_0=1$ (i.e., $H_1$) and $y_0=0$ (i.e., $H_0$). A first difference to standard hypothesis testing is that these hypotheses are not concerned with a property of the data D as a whole (e.g., a summary statistics of D, like its mean), but with the label $y_0$ of the new example $x_0$ that is not part of the training data D. So one can observe one of the two data sets:

$$D_+ = D \cup (1, x_0),$$

$$D_- = D \cup (0, x_0)$$

where $D_+$ is the augmented data set that contains of data actually observed D with hypothetical label $y_0=1$ and $D_-$ is the set if $y_0=0$.

For each of such augmented data sets one can compute the maximal log likelihood. Denote $$w_+^* = \arg\max_w l(w|D_+),$$

$$w_-^* = \arg\max_w l(w|D_-).$$

The probability of label $y_0=1$ predicted for the testing feature vector $x_0$ is $$Pr_G(y_0=1|x_0) = (1+\exp(l(w_+^*|D_+)-l(w_-^*|D_-)))^{-1}.$$

The prediction is computed from the difference in log likelihoods for two augmented data sets that are obtained by joining actual data with one of two possibilities for the testing data.

A procedure according to an embodiment of the invention is as follows. First, for each of m runs: (1) randomly pick a model identified by a parameter vector $w_{true}$ of d dimensions; (2) generate randomly training data D of n d-dimensional feature vectors; (3) generate labels for training feature vectors from the model parameter vector $w_{true}$; (4) compute an MLE estimate $\hat{w}$ of the parameter vector from the training data D; (5) generate k feature vectors for testing; (6) for each of k testing cases $x_i$ compute: (i) the true probability of the label according to the true parameter vector $w_{true}$: $Pr_{true}$; (ii) the probability of the label predicted by MLE: $Pr_{mle}$; (iii) the probability of the label predicted by a method according to an embodiment of the invention $Pr_G$; (iv) the squared errors $(Pr_{mle}-Pr_{true})^2$ and $(Pr_G-Pr_{true})^2$; (7) after m runs the MSE mean square error can be computed.

Experiments of a method according to an embodiment of the invention as described above were run for a list of dimensions from 5 to 50 with step 5. For each value of dimension the number of iterations is m=20. For each iteration, the number of training points is 20 times as many as the dimension: n=20×d. The number of testing points is k=1000.

Figure 11:
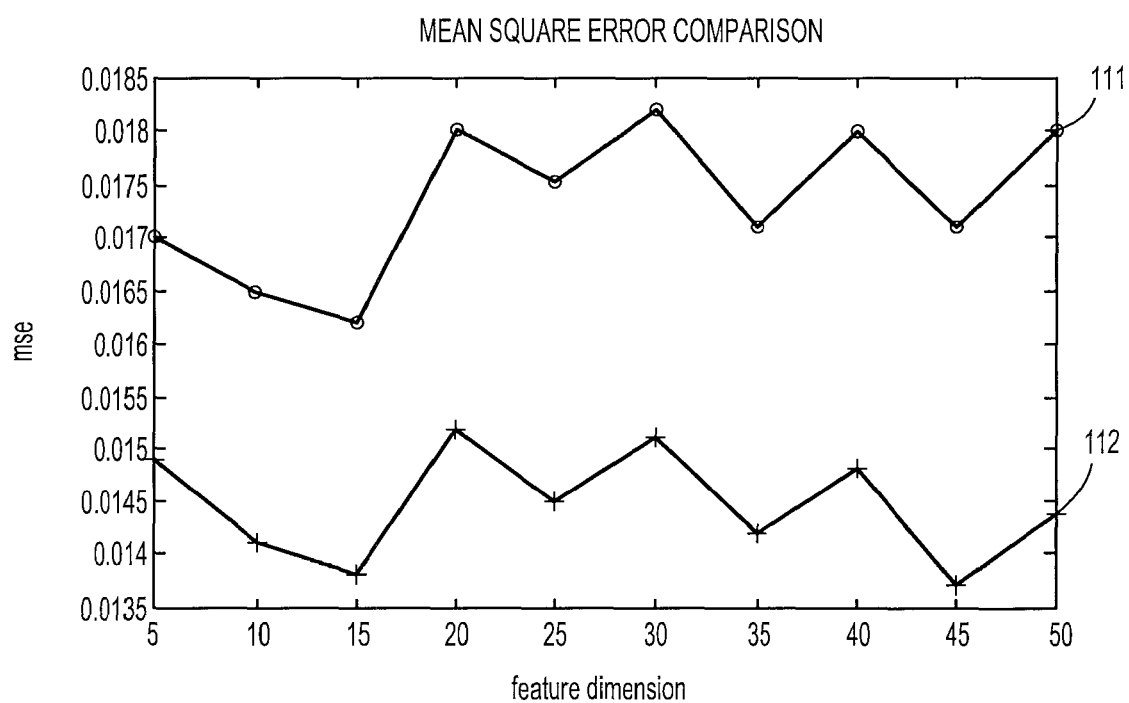
FIG. 11 shows the results of label prediction based on a difference in log likelihoods for two augmented data sets and on MLE, according to an embodiment of the invention.

FIG. 11 shows the results of the two methods. An average mean square error for MLE 111 is 0.01736 and for a method according to an embodiment of the invention 112 is 0.01447. That translates to a prediction of probabilities by MLE that is off by 13.17%, while that of a method according to an embodiment of the invention is off by 12.02%. It is noticeable that this observation holds for whole range of dimensions.

Experiments

Presented herein is a numerical comparison of the following four methods: (1) standard (maximum likelihood) logistic regression (LR), (2) regularized logistic regression (RLR) with standard 2-norm regularization, (3) a LGP approach according to an embodiment of the invention applied to the logistic regression model, and (4) a maximum-a-posteriori odds approach suggested in analogy to an LGP approach according to an embodiment of the invention.

Experiments were performed on five publicly available datasets for the Irvine Machine Learning Database Repository: (1) the Wisconsin Breast Cancer Prognosis—24 months (WPBC 24) dataset (155;32); (2) the Wisconsin Breast Cancer Prognosis—60 months (WPBC 60) dataset (110;32); (3) the ionosphere dataset (351;34); (4) the BUPA Liver Disorders dataset (345;6); and (5) the galaxy dim dataset (4192; 14). The numbers in parenthesis are the dimensions of the datasets: (number of points; number of features).

FIGS. 9(a)-(e) plots the KL divergence of the four methods, logistic regression 91, regularized logistic regression 92, MAP odds approach 93, and a likelihood gamble pricing approach 94 according to an embodiment of the invention, for the five publicly available UCI datasets listed above. The mean and standard deviation of the KL divergence between the real and the predicted values are reported.

Figure 9:
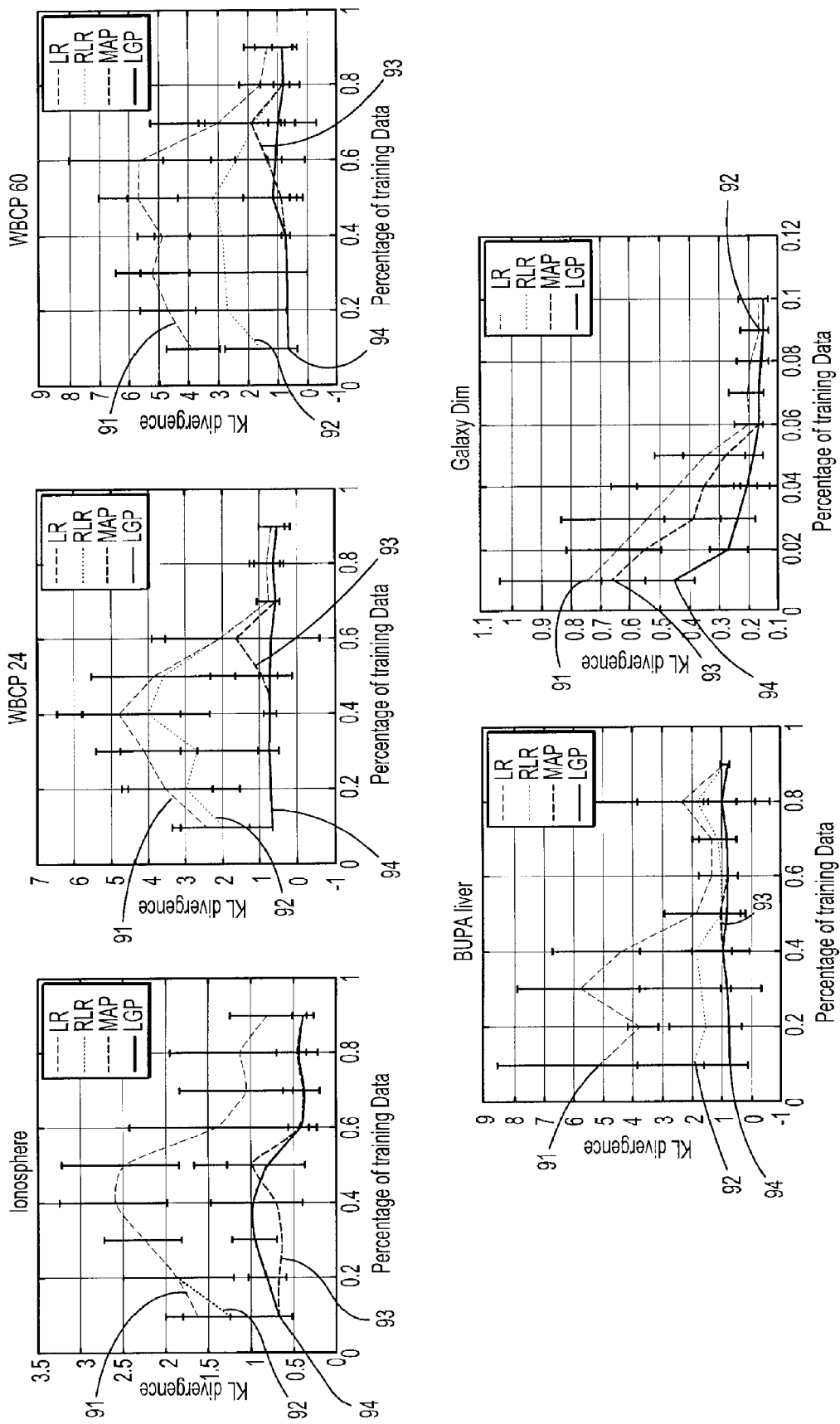
FIGS. 9(a)-(e) plots the KL divergence of the four methods, logistic regression, regularized logistic regression, MAP odds approach, and a likelihood gamble pricing approach according to an embodiment of the invention, for the five publicly available UCI datasets.

The various approaches were evaluated with respect to the continuous valued probability predicted for the labels of (unseen) test-examples, rather than with respect to the binary prediction. Note that this probability is often more meaningful than the binary prediction, e.g., when predicting the probability of a cancer patient for surviving the next 5 years. The standard measures for evaluating the predicted probability in light of the true probability (or empirically observed binary label in the data) of the test-examples are the cross-entropy or the Kullback-Leibler (KL) divergence. Note that the same probability was assigned to each test-example, but normalization issues were ignored, so that the values reported for the KL divergence in FIG. 9 are off by an unknown but irrelevant constant.

For each data set, the prediction accuracy was examined as to how the probability of the label deteriorates as the size of the training-data decreases, as then the importance of the regularization of the prediction increases. For this reason, different sizes of the training data were used, ranging from 10% to 90% of the available data. Since the dim dataset is considerably larger than the other data sets, the training set size was chosen to range from 1% to 10%. The remaining data served as the test data. For each training set size, the experiment was retested 10 times with random partitioning as to obtain an estimate for the mean and standard deviation of the KL divergence, as shown in FIG. 9.

An LPG approach according to an embodiment of the invention as well as the suggested MAP ratio approach consistently make predictions that are closer to the true labels of the test-examples and more robust (less variance) with respect to the empirical KL divergence (compared to the LR and RLR approaches). As the training set size grows, the performances of the various approaches increasingly agree with each other, as expected. These experiments suggest that an LGP approach according to an embodiment of the invention accounts for the ambiguity/uncertainty in the training data, and makes accurate and robust predictions.

Application to Discrete or Continuous-Valued Properties

These models can also be used for predicting discrete or continuous-valued properties, like for instance the probability of 2-year survival of a cancer patient, the probability of re-occurrence of cancer in a patient after a certain time period, or the risk of suffering from a treatment-related side-effect. In case of predicting the probability of 2-year survival of a cancer patient, the training data would be a collection of patients for whom the outcome of 2-year survival is known, as well as several predictors, such as demographics, imaging information, lab results, etc. The new data point is a new patient for whom the probability of 2-year survival has to be predicted.

Figure 10:
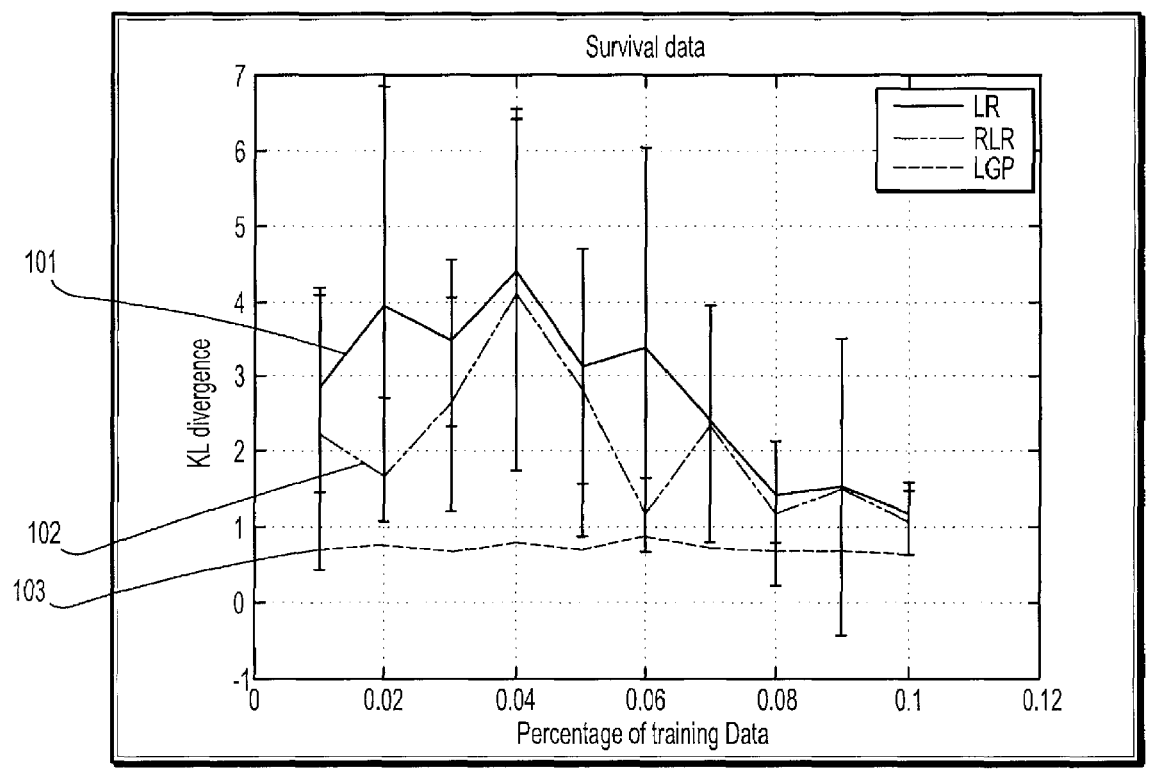
FIG. 10 is a graph of prediction accuracy for 2-year survival measured in terms of KL divergence, according to an embodiment of the invention.

A procedure according to an embodiment of the invention was applied to training data from cancer patients. The objective was to predict the probability of 2-year survival for a test-set of cancer patients. The accuracy of prediction is assessed in terms of the Kullback-Leibler divergence, which is the standard measure of comparing the predicted probability to the observed outcome. FIG. 10 shows results for the KL divergence of the logistic regression 101, regularized logistic regression 102, and a likelihood gamble pricing approach 103 according to an embodiment of the invention. The figure is a graph of prediction accuracy measured in terms of KL divergence, where lower is better: LGP is a procedure according to an embodiment of the invention described above. For comparison: LR is standard maximum likelihood solution to logistic regression, and RLR is the regularized logistic regression method. Note that the shown values of the KL divergence are off by a (irrelevant) constant as normalization issues were ignored.

A method according to an embodiment of the invention as described above is more accurate in predicting the probability of labels than commonly used MLE routine. The method achieves better results than competing methods, especially when the training set is small (i.e., the number of patients is small), as is typically the case in the medical domain. Since a routine to compute maximum log likelihood is implemented in most statistical packages, a method according to an embodiment of the invention does not require any additional implementation and is easy to use.

System Implementations

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 12:
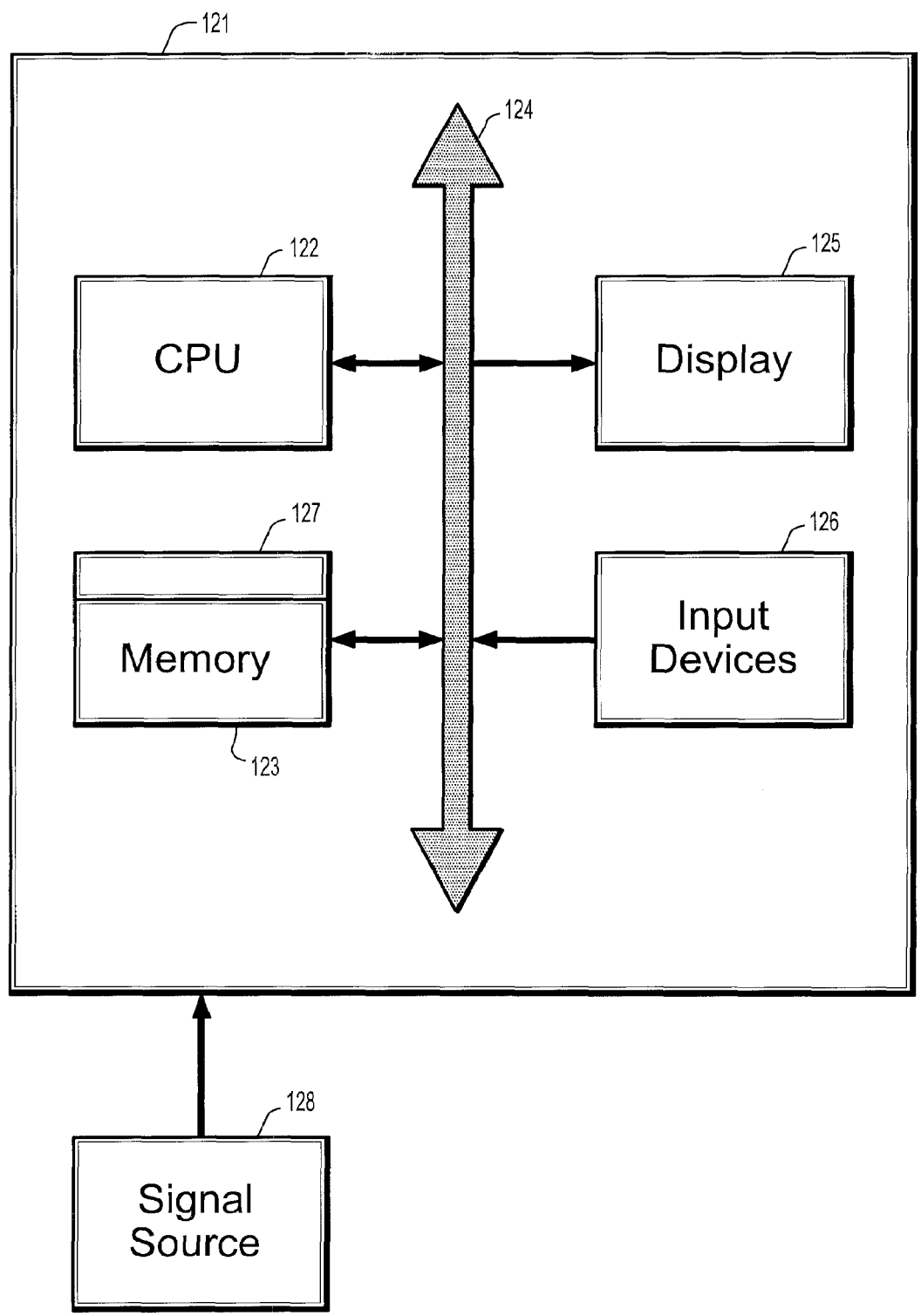
FIG. 12 is a block diagram of an exemplary computer system for implementing a method for the classification of data based on a likelihood gamble pricing approach, according to an embodiment of the invention.

FIG. 12 is a block diagram of an exemplary computer system for implementing a likelihood gamble pricing approach to classification according to an embodiment of the invention. Referring now to FIG. 12, a computer system 121 for implementing the present invention can comprise, inter alia, a central processing unit (CPU) 122, a memory 123 and an input/output (I/O) interface 124. The computer system 121 is generally coupled through the I/O interface 124 to a display 125 and various input devices 126 such as a mouse and a keyboard. The support circuits can include circuits such as cache, power supplies, clock circuits, and a communication bus. The memory 123 can include random access memory (RAM), read only memory (ROM), disk drive, tape drive, etc., or a combinations thereof. The present invention can be implemented as a routine 127 that is stored in memory 123 and executed by the CPU 122 to process the signal from the signal source 128. As such, the computer system 121 is a general purpose computer system that becomes a specific purpose computer system when executing the routine 127 of the present invention.

The computer system 121 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for predicting survival rates of medical patients, said method comprising the steps of:

providing a set D of survival data for a plurality of medical patients having a same condition;

providing a regression model, said model having an associated parameter vector $\beta$;

providing an example $x_0$ of a medical patient whose survival probability is to be classified;

calculating a parameter vector $\hat{\beta}$ that maximizes a log-likelihood function of $\beta$ over the set of survival data, $l(\beta|D)$, wherein the log likelihood $l(\beta|D)$ is a strictly concave function of $\beta$ and is a function of the scalar $x\beta$;

calculating a weight $w_0$ for example $x_0$;

calculating an updated parameter vector $\beta^*$ defined as the parameter vector $\beta$ that maximizes a function $l(\beta|D \cup \{(y_0, x_0, w_0)\})$, wherein data points $(y_0, x_0, w_0)$ augment said set D;

calculating a fair log likelihood ratio $\lambda^f$ from $\hat{\beta}$ and $\beta^*$ using $\lambda^f = \lambda(\beta^*|x_0) + \text{sign}(\lambda(\hat{\beta}|x_0))\{l(\hat{\beta}|D) - l(\beta^*|D)\}$; and mapping the fair log likelihood ratio $\lambda^f$ to a fair price $y_0^f$, wherein said fair price is a probability that class label $y_0$ for example $x_0$ has a value of 1.

2. The method of claim 1, wherein said weight $w_0$ is calculated from $$w_0 = -\frac{\frac{\partial}{\partial(x_0\beta)}|\lambda(\beta|x_0)|}{\frac{\partial}{\partial(x_0\beta)}l(\beta|(y_0, x_0, w_0 = 1))}\bigg|_{\beta=\hat{\beta}},$$

wherein $\lambda(\beta|x_0)$ is a log-likelihood ratio of a likelihood that a class label $y_0$ as a value of 1 over a likelihood that a class label $y_0$ has a value of 0, wherein said log-likelihood-ratio is an affine function of the scalar $x\beta$.

3. The method of claim 2, wherein said regression model is a logistic regression model with a probability of label y being 1 is $$p(y=1\mid x,\beta) = \frac{1}{1+\exp(-\lambda(\beta\mid x))},$$

wherein $\lambda(\beta/x) = x\beta$.

4. The method of claim 3, wherein said log-likelihood of $\beta$ is $$l(\beta\mid D) = \sum_{i=1}^{N} w_i\{(y_i-1)x_i\beta - \log(1+\exp(-x_i\beta))\}.$$

5. The method of claim 3, wherein said weight $w_\diamond$ is calculated from $$w_\diamond = \frac{-\text{sign}(x_\diamond\hat{\beta})}{y_\diamond - 1 + \dfrac{1}{1+\exp(x_\diamond\hat{\beta})}}.$$

6. The method of claim 3, wherein said fair log likelihood ratio $\lambda^f$ is $\lambda^f = x_\diamond\beta^* \text{sign}(x_\diamond\hat{\beta})[l(\hat{\beta}\mid D) - l(\beta^*\mid D)]$.

7. The method of claim 3, wherein said fair price is $$y_\diamond^f = \frac{1}{1+\exp(-\lambda^f)}.$$

8. The method of claim 2, wherein said regression model is a Gaussian regression model with two clusters having a Gaussian distribution for either class, $N(0,\sigma^2)$ and $N(1,\sigma^2)$, wherein $\sigma^2$ is a standard deviation.

9. The method of claim 8, wherein said log-likelihood of $\beta$ is $$l(\beta\mid D) = -\sum_{i=1}^{N} w_i(x_i\beta - y_i)^2/\sigma^2.$$

10. The method of claim 8, wherein said weight $w_\diamond$ is calculated from $$w_\diamond = \frac{-\text{sign}(2x_\diamond\hat{\beta}-1)}{x_\diamond\hat{\beta} - y_\diamond}.$$

11. The method of claim 8, wherein said fair log likelihood ratio $\lambda^f$ is $$\lambda^f = \log\frac{p(y=1\mid x,\beta)}{p(y=0\mid x,\beta)} = (2x\beta-1)/\sigma^2.$$

12. The method of claim 8, wherein said fair price is $$y_\diamond^f = 1 + \lambda^f\sigma^2/2$$

$$= x_\diamond\beta^* + \frac{\text{sign}(2x_\diamond\hat{\beta}-1)}{2}\left(l(\hat{\beta}\mid D) - l(\beta^*\mid D)\right).$$

13. The method of claim 1, wherein said weight $w_0=2$, and said updated parameter vector $\beta^*$ is determined by maximizing $l(\beta\mid D\cup\{(1,x_0,1),(0,x_0,1)\})$, wherein $(1,x_0,1),(0,x_0,1)$ are data points augmenting said set D.

14. A method for predicting survival rates of medical patients, said method comprising the steps of:
provide a set D of survival data for a plurality of medical patients having a same condition;
providing a regression model, said model having an associated parameter vector $\beta$;
providing an example $x_0$ of a medical patient whose survival probability is to be classified;
calculating a first parameter $$l_1 = \max_\beta l(\beta\mid D \cup \{(1, x_\diamond, 1)\})$$

that maximizes a log-likelihood function of $\beta$ over the set of survival data, $l(\beta\mid D)$ augmented by a data point $(1,x_0,1)$, wherein the log likelihood $l(\beta\mid D)$ is a strictly concave function of $\beta$ and is a function of the scalar $x\beta$;
calculating an second parameter $$l_0 = \max_\beta l(\beta\mid D \cup \{(0, x_\diamond, 1)\})$$

that maximizes a log-likelihood function of $\beta$ over the set of survival data, $l(\beta\mid D)$ augmented by a data point $(0,x_0,1)$;
calculating a fair log likelihood ratio $\lambda^f$ from $\lambda^f = l_1 - l_0$; and
mapping the fair log likelihood ratio $\lambda^f$ to a fair price $y_0^f$, wherein said fair price is a probability that class label $y_0$ for example $x_0$ has a value of 1.

15. A non-transitory program storage device readable by a computer, tangibly embodying a program of instructions executable by the computer to perform the method steps for predicting survival rates of medical patients, said method comprising the steps of:
providing a set D of survival data for a plurality of medical patients having a same condition;
providing a regression model, said model having an associated parameter vector fi;
providing an example x:, of a medical patient whose survival probability is to be classified;
calculating a parameter vector/) that maxirnizes a log-likelihood function of fi over the set of survival data, I(/?ID), wherein the log likelihood t(./]ID) is a strictly concave function of fl and is a function of the scalar aft;
calculating a weight w: for example x ; calculating an updated parameter vector fi* defined as the parameter vector fi that maximizes a function t(fll D t.9{(3',:r~,~1;:)}), wherein data points (y: ,x~, ~.;) augment said set D;
calculating a fair log likelihood ratio 2 from /~ and fi* using 2c:=d.(fl* [ a'.)+sign(/~(fl [ a.~)~l(/] I D)−l(fl* t D)}; and
mapping the fair log likelihood ratio 2f to a fair price Y;!l, wherein said fair price is a probability that class label y+ for example x:> has a value of 1.

16. The computer readable program storage device of claim 15, wherein said weight $w_\diamond$ is calculated from $$w_\diamond = -\left.\frac{\frac{\partial}{\partial(x_\diamond\beta)}|\lambda(\beta\,|\,x_\diamond)|}{\frac{\partial}{\partial(x_\diamond\beta)}l(\beta\,|\,(y_\diamond,x_\diamond,w_\diamond=1))}\right|_{\beta=\hat\beta},$$

wherein $\lambda(\beta|x_0)$ is a log-likelihood ratio of a likelihood that a class label $y_0$ has a value of 1 over a likelihood that a class label $y_0$ has a value of 0, wherein said log-likelihood-ratio is an affine function of the scalar $x\beta$.

17. The computer readable program storage device of claim 16, wherein said regression model is a logistic regression model with a probability of label y being 1 is $$p(y=1\,|\,x,\beta) = \frac{1}{1+\exp(-\lambda(\beta\,|\,x))}, \text{ wherein } \lambda(\beta\,|\,x) = x\beta.$$

18. The computer readable program storage device of claim 17, wherein said log-likelihood of β is $$l(\beta\,|\,D) = \sum_{i=1}^{N} w_i\{(y_i-1)x_i\beta - \log(1+\exp(-x_i\beta))\}.$$

19. The computer readable program storage device of claim 17, wherein said weight $w_0$ is calculated from $$w_\diamond = \frac{-\text{sign}(x_\diamond\hat\beta)}{y_\diamond - 1 + \frac{1}{1+\exp(x_\diamond\hat\beta)}}.$$

20. The computer readable program storage device of claim 17, wherein said fair log likelihood ratio $\lambda^f$ is $\lambda^f = x_0\beta^* + \text{sign}(x_0\hat\beta)\lfloor l(\hat\beta|D) - l(\beta^*|D)\rfloor$.

21. The computer readable program storage device of claim 17, wherein said fair price is $$y_\diamond^f = \frac{1}{1+\exp(-\lambda^f)}.$$

22. The computer readable program storage device of claim 16, wherein said regression model is a Gaussian regression model with two clusters having a Gaussian distribution for either class, $N(0,\sigma^2)$ and $N(1,\sigma^2)$, wherein $\sigma^2$ is a standard deviation.

23. The computer readable program storage device of claim 22, wherein said log-likelihood of β is $$l(\beta\,|\,D) = -\sum_{i=1}^{N} w_i(x_i\beta - y_i)^2/\sigma^2.$$

24. The computer readable program storage device of claim 22, wherein said weight $w_0$ is calculated from $$w_\diamond = \frac{-\text{sign}(2x_\diamond\hat\beta - 1)}{x_\diamond\hat\beta - y_\diamond}.$$

25. The computer readable program storage device of claim 22, wherein said fair log likelihood ratio $\lambda^f$ is $$\lambda^f = \log\frac{p(y=1\,|\,x,\beta)}{p(y=0\,|\,x,\beta)} = (2x\beta-1)/\sigma^2.$$

26. The computer readable program storage device of claim 23, wherein said fair price is $$y_\diamond^f = 1 + \lambda^f\sigma^2/2$$
$$= x_\diamond\beta^* + \frac{\text{sign}(2x_\diamond\hat\beta-1)}{2}\bigl(l(\hat\beta\,|\,D) = l(\beta^*\,|\,D)\bigr).$$

27. The computer readable program storage device of claim 15, wherein said weight $w_0=2$, and said updated parameter vector $\beta^*$ is determined by maximizing $l(\beta|D\cup\{(1,x_0,1),(0,x_0,1)\})$, wherein $(1,x_0,1),(0,x_0,1)$ are data points augmenting said set D.

* * * * *